United States Patent
Rohde et al.

(10) Patent No.: US 12,016,281 B2
(45) Date of Patent: Jun. 25, 2024

(54) PLANTS COMPRISING WHEAT G-TYPE CYTOPLASMIC MALE STERILITY RESTORER GENES, MOLECULAR MARKERS AND USES THEREOF

(71) Applicant: BASF SE, Ludwigshafen am Rhein (DE)

(72) Inventors: Antje Rohde, Ghent (BE); John Jacobs, Merelbeke (BE)

(73) Assignee: BASF SE, Ludwigshafen am Rhein (DE)

( * ) Notice: Subject to any disclaimer, the term of this patent is extended or adjusted under 35 U.S.C. 154(b) by 324 days.

(21) Appl. No.: 16/085,442

(22) PCT Filed: Mar. 16, 2017

(86) PCT No.: PCT/EP2017/056306
§ 371 (c)(1),
(2) Date: Sep. 14, 2018

(87) PCT Pub. No.: WO2017/158128
PCT Pub. Date: Sep. 21, 2017

(65) Prior Publication Data
US 2019/0082628 A1 Mar. 21, 2019

(30) Foreign Application Priority Data

Mar. 16, 2016 (EP) ..................... 16160773
Jul. 18, 2016 (EP) ..................... 16180022

(51) Int. Cl.
| | | |
|---|---|---|
| A01H 1/02 | (2006.01) | |
| A01H 1/04 | (2006.01) | |
| C07K 14/415 | (2006.01) | |
| C12N 15/82 | (2006.01) | |
| C12Q 1/6895 | (2018.01) | |

(52) U.S. Cl.
CPC ............. *A01H 1/023* (2021.01); *A01H 1/045* (2021.01); *C07K 14/415* (2013.01); *C12N 15/8287* (2013.01); *C12N 15/8289* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

FOREIGN PATENT DOCUMENTS

| | | | |
|---|---|---|---|
| EP | 3336196 A1 | 6/2018 | |
| EP | 3575417 A1 | 12/2019 | |
| EP | 3718397 A1 | 10/2020 | |
| WO | 2019086510 A1 | 5/2019 | |

OTHER PUBLICATIONS

Zhang et al., 2003, "Location of the Fertility Restorer Gene for T-Type CMS Wheat by Microsatellite Marker", Acta Genetica Sinica 30 (5): 459-464; English translation.*
USDA PVP 7400045 certificate for wheat DeKalb 582M, Dec. 11, 1973.*
Zhang et al (2003, "Location of the Fertility Restorer Gene for T-Type CMS Wheat by Microsatellite Marker", Acta Genetica Sinica 30 (5): 459-464).*
Zhang et al (2003, "Location of the Fertility Restorer Gene for T-Type CMS Wheat by Microsatellite Marker", Acta Genetica Sinica 30 (5): 459-464; English translation). (Year: 2003).*
"*Triticum aestivum* L. subsp. *Aestivum*", PI 583676, U.S. National Plant Germplasm System, XP2770568, 1994, 1 page.
Ahmed, et al., "QTL analysis of fertility-restoration against cytoplasmic male sterility in wheat", Genes and Genetic Systems, vol. 76, Issue 1, 2001, pp. 33-38.
Bahl, et al., "Chromosomal Location of Male Fertility Restoring Genes in Six Lines of Common Wheat", Crop Science Abstract, vol. 13, Issue 3, 1973, pp. 317-320.
Database PVPO—Certificate Status [Online], XP002770567, Database accession No. 7400045, Oct. 17, 1975, 16 pages.
Du, et al., "Genetic Analyses of Male-Fertility Restoration in Wheat: III. Effects of Aneuploidy", Crop Science Abstract, vol. 31, Issue 2, 1991, pp. 319-322.
F. A. Lilienfeld, "H. Kihara: Genome-Analysis in Triticum and Aegilops. X: Concluding Review", Cytologia, vol. 16, Issue 2, 1951, pp. 101-123.
G. C. M. Sage, "Nucleo-cytoplasmic relationships in wheat", Advances in Agronomy, vol. 28, 1976, pp. 265-298.
Hedgcoth, et al., "A chimeric open reading frame associated with cytoplasmic male sterility in alloplasmic wheat with Triticum timopheevi mitochondria is present in several *Triticum* and *Aegilops* species, barley, and rye", Current Genetics, vol. 41, Issue 5, Aug. 2002, pp. 357-366.
International Search Report for PCT Patent Application No. PCT/EP2017/056306, dated Aug. 11, 2017, 5 pages.
Kojima, et al., "High-resolution RFLP mapping of the fertility restoration (Rf3) gene against Triticum timopheevi cytoplasm located on chromosome 1BS of common wheat", Genes and Genetic Systems, vol. 72, Issue 6, 1997, pp. 353-359.
Ma, et al., "Genetic Analysis of Fertility Restoration in Wheat Using Restriction Fragment Length Polymorphisms", Crop Science, vol. 35, Issue 4, Jul. 1995, pp. 1137-1143.
Mohan L. H. Kaul, "Male Sterility in Higher Plants", Monographs on Theoretical and Applied Genetics, vol. 10, Issue 1, 1988, 1005 pages.
Mukai, et al., "Basic studies on hybrid wheat breeding", Theoretical and Applied Genetics, vol. 54, Issue 4, Jul. 1979, pp. 153-160.
Robertson, et al., "Monosomic Analysis of Fertility-Restoration in Common Wheat (*Triticum aestivum* L.)", Crop Science Abstract, vol. 7, Issue 5, 1967, pp. 493-495.

(Continued)

*Primary Examiner* — Charles Logsdon
(74) *Attorney, Agent, or Firm* — ArentFox Schiff LLP

(57) ABSTRACT

Methods are described for selecting or producing a cereal plant comprising functional restorer genes for wheat G-type cytoplasmic male sterility and nucleic acids for use therein.

10 Claims, 3 Drawing Sheets

Figure 1:
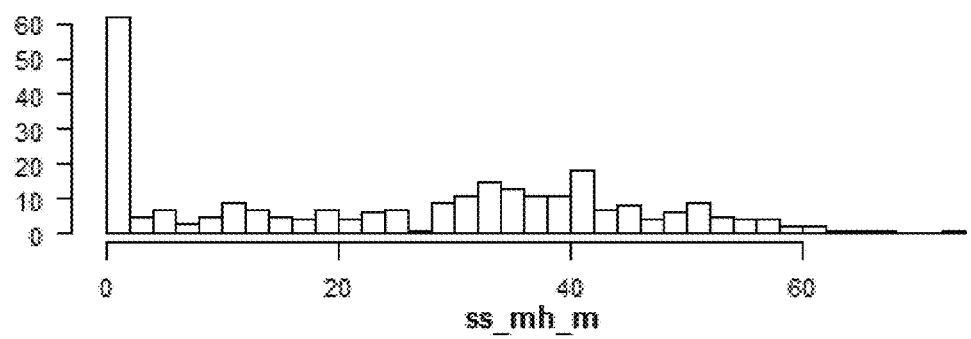
Figure 1:
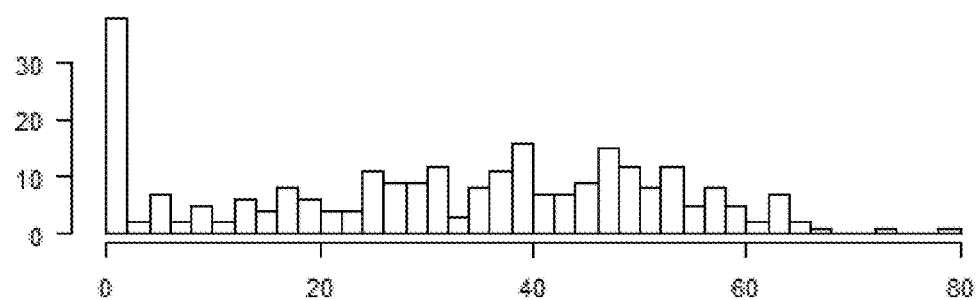

Specification includes a Sequence Listing.

(56) References Cited

OTHER PUBLICATIONS

Sinha, et al., "Genetic analysis and molecular mapping of a new fertility restorer gene Rf8 for Triticum timopheevi cytoplasm in wheat (*Triticum aestivum* L.) using SSR markers", Genetica, vol. 141, Issue 10-12, Oct. 2013, pp. 431-441.

Song, et al., "Influence of nuclear background on transcription of a chimeric gene (orf256) and coxl in fertile and cytoplasmic male sterile wheats", Genome, vol. 37, Issue 2, 1994, pp. 203-209.

Tahir, et al., "Monosomic analysis of *Triticum spelta* var. *duhamelianum*, a fertility-restorer for T. timopheevi cytoplasm", The Japanese Journal of Genetics, vol. 44, Issue 1, Jan. 1969, pp. 1-9.

Tsunewaki, et al., "Plasmon analysis of *Triticum* (wheat) and Aegilops. 1. Production of alloplasmic common wheats and their fertilities", Genes & Genetic Systems, vol. 71, Issue 5, 1996, pp. 293-311.

Zhang, et al., "Location of the fertility restorer gene for T-type CMS wheat by Microsatellite Marker", Acta Genetica Sinica, vol. 30, Issue 5, May 2003, pp. 459-464.

Zhou, et al., "SSR markers associated with fertility restoration genes against Triticum timopheevii cytoplasm in Triticum aestivum", Euphytica, vol. 141, Issue 1-2, Jan. 2005, pp. 33-40.

Geyer et al., "Exploring the genetics of fertility restoration controlled by Rf1 in common wheat (*Triticum aestivum* L.) using high-density linkage maps," Molecular Genetics and Genomics (2018) 293, pp. 451-462.

Geyer et al., "Distribution of the fertility-restoring gene Rf3 in common and spelt wheat determined by an informative SNP marker," Mol breeding (2016) 36: 167, pp. 1-11.

Würschum et al., "Genetic architecture of male fertility restoration of Triticum timopheevii cytoplasm and fine-mapping of the major restorer locus Rf3 on chromosome 1B," Theor Appl Genet (2017) 130, pp. 1253-1266.

* cited by examiner

PLANTS COMPRISING WHEAT G-TYPE CYTOPLASMIC MALE STERILITY RESTORER GENES, MOLECULAR MARKERS AND USES THEREOF

CROSS REFERENCE TO RELATED APPLICATIONS

This application is a 35 U.S.C. § 371 National Phase of PCT Application No. PCT/EP2017/056306 filed Mar. 16, 2017, which claims priority to EP Application No. 16180022.2 filed Jul. 18, 2016 and EP Application No. 16160773.4 filed Mar. 16, 2016, the disclosures of which are hereby incorporated by reference in their entireties.

FIELD OF THE INVENTION

The present invention relates generally to the field of plant breeding and molecular biology and concerns a method for selecting or producing a cereal plant comprising a functional restorer gene for wheat G-type cytoplasmic male sterility, and nucleic acids for use therein.

BACKGROUND

Cytoplasmic male sterility (CMS) is a major trait of interest in cereals such as wheat in the context of commercial hybrid seed production (Kihara, 1951; Wilson and Ross, 1962; Lucken, 1987; Sage, 1976). The cytoplasms of *Triticum timopheevi* (G-type) and *Aegilops kotschyi* (K-type) are widely studied as inducers of male sterility in common wheat (*Triticum aestivum*), due to few deleterious effects (Kaul, 1988; Lucken, 1987; Mukai and Tsunewaki, 1979).

In hybrid seed production system using the G-type cytoplasm, fertility restoration is a critical problem. Most of the hexaploid wheats do not naturally contain fertility restoration genes (Ahmed et al. Genes Genet. Syst. 2001). In the complicated restoration system of *T. timopheevi*, eight Rf genes are reported to restore the fertility against *T. timopheevii* cytoplasm, and their chromosome locations have been determined, namely, Rf1 (1A), Rf2 (7D), Rf3 (1B), Rf4 (6B), Rf5 (6D), Rf6 (5D), Rf7 (7B) and Rf8 (Tahir & Tsunewaki, 1969; Yen et al., 1969; Bahl & Maan, 1973; Du et al., 1991; Sihna et al., 2013). Ma et al. (1991) transferred an Rf gene from *Aegilops umbellulata* to wheat, the gene being located on chromosomes 6AS and 6BS (from Zhou et al., 2005).

Zhang et al., (Acta Genetica *Sinica* 06/2003; 30(5):459-64.) describe an Rf locus located on 1AS in restorer line 7269-10, with the genetic distance between the SSR marker Xgwm136 and this Rf gene being 6.7 cM.

Ma and Sorrels (Crop Science 1995) reported the linkage of Rf3 to RFLP markers Xbcd249 and Xcdo442 on chromosome 1BS.

Kojima (Genes Genet Syst 1997) localized a fertility restorer gene from Chinese Spring termed Rf3 gene at a position 1.2 cM and 2.6 cM distant from RFLP markers Xcdo388 and Xabc156, respectively, although the authors were able to separate Rf3 from Xcdo388. It was estimated that that Rf3 could exist within a region of 500 Kbp of the adjacent RFLP markers.

Ahmed Talaat et al (Genes Genet. Syst., 2001) determined the close linkage of a major Rf QTL against G-type cytoplasm on chromosome 1B with RFLP marker XksuG9c, close to marker Xabc156 as reported by Kojima et al (supra).

Zhang et al., (Yi Chuan Xue Bao 2003) describe an Rf gene located on 1BS with a genetic distance of 5.1 cM to microsatellite marker Xgwm550.

Zhou et al (2005) describe Rf3 gene to be located either between SSR markers Xgwm582 and Xbarc207 or between Xbarc207 and Xgwm131 but very close to Xbarc207. Since the previously identified RFLP markers of Kojima, Ahmed and Ma & Sorrels were not mapped in their mapping population, a linkage map including these RFLP markers could not be constructed to better estimate the distance between Rf3 and the identified SSR markers.

Accordingly, there remains the need for more accurate markers to identify and track Rf loci in breeding, which are particularly useful for hybrid seed production, and for improved methods for fertility restoration in wheat *Thimopheevi* cytoplasm. The present invention provides a contribution over the art by disclosing the location of functional Rf genes on chromosome 1A and 1B and by providing markers that are more accurate and/or more tightly linked to the causal genes.

SUMMARY

A method is described for selecting a cereal plant comprising a functional restorer gene allele for wheat G-type cytoplasmic male sterility located on chromosome 1A (1A restorer gene allele) and a functional restorer gene allele for wheat G-type cytoplasmic male sterility located on chromosome 1B (1B restore gene allele) OR for producing a cereal plant comprising a functional restorer gene allele for wheat G-type cytoplasmic male sterility located on chromosome 1A (1A restorer gene allele) and a functional restorer gene allele for wheat G-type cytoplasmic male sterility located on chromosome 1B (1B restorer gene allele), comprising the steps of:
  (a) identifying at least one cereal plant comprising at least one marker allele linked to a functional restorer gene allele for wheat G-type cytoplasmic male sterility located on chromosome 1A (1A restorer marker allele) and at least one marker allele linked to a functional restorer gene allele for wheat G-type cytoplasmic male sterility located on chromosome 1B (1B restorer marker allele); and
  (b) selecting the plant comprising said at least one 1A restorer marker allele and said at least one 1B restorer marker allele, wherein said plant comprises said 1A restorer gene allele and said 1B restorer gene allele,
  wherein said at least one 1A restorer marker allele localises within an interval on chromosome 1A comprising and flanked by the markers of SEQ ID NO 2 and SEQ ID NO 4 and said at least one 1B restorer marker allele localises within an interval on chromosome 1B comprising and flanked by the markers of SEQ ID NO 7 and SEQ ID NO 13.

Further, a method is described for restoring fertility in a progeny of a G-type cytoplasmic male sterile cereal plant or for producing a fertile progeny plant from a G-type cytoplasmic male sterile cereal parent plant, comprising the steps of:
  (a) Providing a population of progeny plants obtained from crossing a female cereal parent plant with a male cereal parent plant, wherein the female parent plant is a G-type cytoplasmic male sterile cereal plant, and wherein the male parent plant comprises a functional restorer gene allele for wheat G-type cytoplasmic male sterility located on chromosome 1A (1A restorer gene allele) and a functional restorer gene allele for wheat G-type cytoplasmic male sterility located on chromosome 1B (1B restorer gene allele);
(b) Identifying in said population a fertile progeny plant comprising at least one marker allele linked to said functional restorer gene allele for wheat G-type cytoplasmic male sterility located on chromosome 1A (1A restorer marker allele) and at least one marker allele linked to said functional restorer gene allele for wheat G-type cytoplasmic male sterility located on chromosome 1B (1B restorer marker allele), wherein said progeny plant comprises said 1A restorer gene allele and said 1B restorer gene allele; optionally
(c) Selecting said fertile progeny plant; and optionally
(d) Propagating the fertile progeny plant,
wherein said at least one 1A marker allele localises within an interval on chromosome 1A comprising and flanked by the markers of SEQ ID NO 2 and SEQ ID NO 4 and said at least one 1B marker allele localises within an interval on chromosome 1B comprising and flanked by the markers of SEQ ID NO 7 and SEQ ID NO 13.

The at least one 1A marker allele can be selected from any one of:
a. An A at SEQ ID NO: 2;
b. a C at SEQ ID NO: 3;
c. a C at SEQ ID NO: 4;
d. a C at SEQ ID NO: 16;
e. a G at SEQ ID NO: 17;
f. a C at SEQ ID NO: 18;
g. a G at SEQ ID NO: 19;
or any combination thereof;
and/or the at least one 1B marker allele can be selected from any one of:
h. a T at SEQ ID NO: 7;
i. a C at SEQ ID NO: 8;
j. a T at SEQ ID NO: 9;
k. a T at SEQ ID NO: 10;
l. an A at SEQ ID NO: 11;
m. an A at SEQ ID NO: 12;
n. a G at SEQ ID NO: 13;
o. a C at SEQ ID NO: 22;
p. an A at SEQ ID NO: 23,
q. a T at SEQ ID NO: 24;
r. a T at SEQ ID NO: 25,
or any combination thereof.

The at least one 1A marker allele can also localise to an interval on chromosome 1A comprising and flanked by the marker pair of SEQ ID NO: 16 and SEQ ID NO: 19 and/or the at least one 1B marker allele can localise to an interval on chromosome 1B comprising and flanked by the marker pair of SEQ ID NO: 22 and SEQ ID NO: 25.

The at least one 1A restorer marker allele can also be selected from any one of:
a. a C at SEQ ID NO: 16;
b. a G at SEQ ID NO: 17;
c. a C at SEQ ID NO: 18;
d. a G at SEQ ID NO: 19;
or any combination thereof;
and/or wherein said at least one 1B restorer marker allele is selected from any one of:
e. a C at SEQ ID NO: 22;
f. an A at SEQ ID NO: 23,
g. a T at SEQ ID NO: 24;
h. a T at SEQ ID NO: 25,
or any combination thereof.

The at least one 1A restorer marker allele can also be a C at SEQ ID NO. 18 and/or said at least one 1B restorer marker allele can be a T at SEQ ID NO. 24.

The 1A restorer gene allele and/or said 1B functional restorer gene allele can be obtainable from USDA accession number PI 583676.

Further, a method is described for producing a cereal plant comprising a functional restorer gene allele for wheat G-type cytoplasmic male sterility located on chromosome 1A and a functional restorer gene allele for wheat G-type cytoplasmic male sterility located on chromosome 1B, comprising the steps of
a. crossing a first cereal plant comprising a functional restorer gene for wheat G-type cytoplasmic male sterility located on chromosome 1A and comprising a functional restorer gene for wheat G-type cytoplasmic male sterility located on chromosome 1B with a second cereal plant
b. identifying a progeny plant comprising a functional restorer gene allele for wheat G-type cytoplasmic male sterility located on chromosome 1A and comprising a functional restorer gene allele for wheat G-type cytoplasmic male sterility located on chromosome 1B according to any of the methods described herein.

Further, a method is described for producing a cereal plant comprising a functional restorer gene allele for wheat G-type cytoplasmic male sterility located on chromosome 1A and comprising a functional restorer gene allele for wheat G-type cytoplasmic male sterility located on chromosome 1B, comprising the steps of
a. crossing a first cereal plant homozygous for a functional restorer gene for wheat G-type cytoplasmic male sterility located on chromosome 1A and homozygous for a functional restorer gene for wheat G-type cytoplasmic male sterility located on chromosome 1B with a second cereal plant
b. obtaining a progeny plant, wherein said progeny plant comprises a functional restorer gene allele for wheat G-type cytoplasmic male sterility located on chromosome 1A and a functional restorer gene allele for wheat G-type cytoplasmic male sterility located on chromosome 1B Further, a method is described for producing hybrid seed, comprising the steps of:
a. Providing a male cereal parent plant comprising at least one marker allele linked to a functional restorer gene for wheat G-type cytoplasmic male sterility located on chromosome 1A and at least one marker allele linked to a functional restorer gene for wheat G-type cytoplasmic male sterility located on chromosome 1B as described in any one of claims 1-7, said male parent plant comprising said functional restorer gene allele for wheat G-type cytoplasmic male sterility located on chromosome 1A and said functional restorer gene for wheat G-type cytoplasmic male sterility located on chromosome 1B as described in any one of claims 1-7, preferably either one or both in homozygous form.
b. Providing a female cereal parent plant that is a G-type cytoplasmic male sterile cereal plant.
c. Crossing said female cereal parent plant with a said male cereal parent plant; and optionally
d. Harvesting seeds.

The first plant or said male parent plant can have been selected according to the method of any one of claims 1-7.

Further, a method is described for determining the presence or absence or zygosity status of a functional restorer gene allele for wheat G-type cytoplasmic male sterility located on chromosome 1A and the presence or absence or zygosity status of a functional restorer gene allele for wheat G-type cytoplasmic male sterility located on chromosome 1B in a biological sample, comprising the steps of
  a. providing genomic DNA from said biological sample, and
  b. analysing said DNA for the presence or absence or zygosity status of at least one marker allele linked to said functional restorer gene for wheat G-type cytoplasmic male sterility located on chromosome 1A (1A restorer marker allele) and the presence of at least one marker allele linked to said functional restorer gene for wheat G-type cytoplasmic male sterility located on chromosome 1B (1B restorer marker allele),
  wherein said at least one 1A restorer marker allele localises within an interval on chromosome 1A/1B comprising and flanked by the markers of SEQ ID NO 2 and SEQ ID NO 4 and said at least one 1B restorer marker allele localises within an interval on chromosome 1B comprising and flanked by the markers of SEQ ID NO 7 and SEQ ID NO 13 as described in any one of claims 1-7.

Also described is a cereal plant, plant part, plant cell or seed comprising at least one functional restorer gene allele for wheat G-type cytoplasmic male sterility located on chromosome 1A and at least one functional restorer gene allele for wheat G-type cytoplasmic male sterility located on chromosome 1B, said plant comprising at least one marker allele linked to a functional restorer gene allele for wheat G-type cytoplasmic male sterility located on chromosome 1A (1A restorer marker allele), wherein said at least one marker allele localises within an interval on chromosome 1A comprising and flanked by the markers of SEQ ID NO. 2 and 4, preferably wherein said plant comprises at least one of, preferably wherein said plant comprises one or more of:
  a. an A at SEQ ID NO: 2;
  b. a C at SEQ ID NO: 3;
  c. a C at SEQ ID NO: 4;
  d. a C at SEQ ID NO: 16;
  e. a G at SEQ ID NO: 17;
  f. a C at SEQ ID NO: 18;
  g. a G at SEQ ID NO: 19;
  said plant not comprising any one or all of:
  h. a G at SEQ ID NO: 1;
  l. an A at SEQ ID NO: 5;
  said plant further comprising at least one marker allele linked to a functional restorer gene allele for wheat G-type cytoplasmic male sterility located on chromosome 1B (1B restorer marker allele), wherein said at least one marker allele localises within an interval on chromosome 1B comprising and flanked by the markers of SEQ ID NO: 7 and 13, preferably wherein said plant comprises one or more of:
  j. a T at SEQ ID NO: 7;
  k. a C at SEQ ID NO: 8;
  i. a T at SEQ ID NO: 9;
  m. a T at SEQ ID NO: 10;
  n. an A at SEQ ID NO: 11;
  o. an A at SEQ ID NO: 12;
  p. a G at SEQ ID NO: 13;
  q. a C at SEQ ID NO: 22;
  r. an A at SEQ ID NO: 23,
  s. a T at SEQ ID NO: 24;
  t. a T at SEQ ID NO: 25,
  said plant not comprising any one or all of:
  u. an A at SEQ ID NO: 6;
  v. a T at SEQ ID NO: 14.

Thus, also described is a cereal plant, plant part, plant cell or seed comprising at least one functional restorer gene allele for wheat G-type cytoplasmic male sterility located on chromosome 1A and at least one functional restorer gene allele for wheat G-type cytoplasmic male sterility located on chromosome 1B, said plant comprising at least one of (such as one, two, three, four, five, six, or all of):
  a. An A at SEQ ID NO: 2;
  b. a C at SEQ ID NO: 3;
  c. a C at SEQ ID NO: 4;
  d. a C at SEQ ID NO: 16;
  e. a G at SEQ ID NO: 17;
  f. a C at SEQ ID NO: 18;
  g. a G at SEQ ID NO: 19;
  said plant not comprising any one or all of:
  h. a G at SEQ ID NO: 1;
  l. an A at SEQ ID NO: 5;
  said plant further comprising at least one of (such as one, two, three, four, five, six, seven, eight, nine, ten or all of):
  j. a T at SEQ ID NO: 7;
  k. a C at SEQ ID NO: 8;
  l. a T at SEQ ID NO: 9;
  m. a T at SEQ ID NO: 10;
  n. an A at SEQ ID NO: 11;
  o. an A at SEQ ID NO: 12;
  p. a G at SEQ ID NO: 13;
  q. a C at SEQ ID NO: 22;
  r. an A at SEQ ID NO: 23,
  s. a T at SEQ ID NO: 24;
  t. a T at SEQ ID NO: 25,
  said plant not comprising any one or all of:
  u. an A at SEQ ID NO: 6;
  v. a T at SEQ ID NO: 14.

Also described is a cereal plant, plant part, plant cell or seed comprising at least one functional restorer gene allele for wheat G-type cytoplasmic male sterility located on chromosome 1A and at least one functional restorer gene allele for wheat G-type cytoplasmic male sterility located on chromosome 1B, said plant comprising at least one marker allele linked to a functional restorer gene allele for wheat G-type cytoplasmic male sterility located on chromosome 1A (1A restorer marker allele), wherein said at least one marker allele localises within an interval on chromosome 1A comprising and flanked by the markers of SEQ ID NO. 16 and 19, preferably wherein said plant comprises one or more of:
  a. a C at SEQ ID NO: 16;
  b. a G at SEQ ID NO: 17;
  c. a C at SEQ ID NO: 18;
  d. a G at SEQ ID NO: 19;
  said plant not comprising any one or all of
  e. an A at SEQ ID NO: 2;
  f. a C at SEQ ID NO: 4;
  said plant further comprising at least one marker allele linked to a functional restorer gene allele for wheat G-type cytoplasmic male sterility located on chromosome 1B (1B restorer marker allele), wherein said at least one marker allele localises within an interval on chromosome 1B comprising and flanked by the markers of SEQ ID NO. 22 and 25, preferably wherein said plant comprises one or more of:
  g. a C at SEQ ID NO: 22;
  h. an A at SEQ ID NO: 23,
  i. a T at SEQ ID NO: 24;
  j. a T at SEQ ID NO: 25,
  said plant not comprising any one or all of
  k. a T at SEQ ID NO: 7;
  l. an G at SEQ ID NO: 13.

Thus, also described is a cereal plant, plant part, plant cell or seed comprising at least one functional restorer gene allele for wheat G-type cytoplasmic male sterility located on chromosome 1A and at least one functional restorer gene allele for wheat G-type cytoplasmic male sterility located on chromosome 1B, said plant comprising at least one of (such as one, two, three or all of):
a. a C at SEQ ID NO: 16;
b. a G at SEQ ID NO: 17;
c. a C at SEQ ID NO: 18;
d. a G at SEQ ID NO: 19;
said plant not comprising any one or all of
e. an A at SEQ ID NO: 2;
f. a C at SEQ ID NO: 4;
said plant further comprising at least one of (such as one, two, three or all of):
g. a C at SEQ ID NO: 22;
h. an A at SEQ ID NO: 23,
i. a T at SEQ ID NO: 24;
j. a T at SEQ ID NO: 25,
said plant not comprising any one or all of
k. a T at SEQ ID NO: 7;
l. an G at SEQ ID NO: 13.

Also described is a cereal plant, plant part, plant cell or seed comprising at least one functional restorer gene allele for wheat G-type cytoplasmic male sterility located on chromosome 1A and at least one functional restorer gene allele for wheat G-type cytoplasmic male sterility located on chromosome 1B, said plant comprising at least one marker allele linked to a functional restorer gene allele for wheat G-type cytoplasmic male sterility located on chromosome 1A (1A restorer marker allele), wherein said at least one marker allele localises within an interval on chromosome 1A comprising and flanked by the markers of SEQ ID NO. 16 and 19, preferably wherein said plant comprises one or more of:
a. a C at SEQ ID NO: 16;
b. a G at SEQ ID NO: 17;
c. a C at SEQ ID NO: 18;
d. a G at SEQ ID NO: 19;
said plant not comprising any one or all of
e. a T at SEQ ID NO: 15;
f. a C at SEQ ID NO: 20;
said plant further comprising at least one marker allele linked to a functional restorer gene allele for wheat G-type cytoplasmic male sterility located on chromosome 1B (1B restorer marker allele), wherein said at least one marker allele localises within an interval on chromosome 1B comprising and flanked by the markers of SEQ ID NO. 22 and 25, preferably wherein said plant comprises one or more of:
g. a C at SEQ ID NO: 22;
h. an A at SEQ ID NO: 23,
i. a T at SEQ ID NO: 24;
j. a T at SEQ ID NO: 25,
said plant not comprising any one or all of
k. a T at SEQ ID NO: 21;
l. a T at SEQ ID NO: 10.

Thus, also described is a cereal plant, plant part, plant cell or seed comprising at least one functional restorer gene allele for wheat G-type cytoplasmic male sterility located on chromosome 1A and at least one functional restorer gene allele for wheat G-type cytoplasmic male sterility located on chromosome 1B, said plant comprising at least one of (such as one, two, three or all of):
a. a C at SEQ ID NO: 16;
b. a G at SEQ ID NO: 17;
c. a C at SEQ ID NO: 18;
d. a G at SEQ ID NO: 19;
said plant not comprising any one or all of
e. a T at SEQ ID NO: 15;
f. a C at SEQ ID NO: 20;
said plant further comprising at least one of (such as one, two, three or all of):
g. a C at SEQ ID NO: 22;
h. an A at SEQ ID NO: 23,
i. a T at SEQ ID NO: 24;
j. a T at SEQ ID NO: 25,
said plant not comprising any one or all of
k. a T at SEQ ID NO: 21;
l. a T at SEQ ID NO: 10.

Also described is a cereal plant, plant part, plant cell or seed comprising at least one functional restorer gene allele for wheat G-type cytoplasmic male sterility located on chromosome 1A and at least one functional restorer gene allele for wheat G-type cytoplasmic male sterility located on chromosome 1B, said plant comprising a C at SEQ ID NO. 18 and/or a T at SEQ ID NO. 24, said plant not comprising any one or all of a C at SEQ ID NO: 16; a G at SEQ ID NO: 17; a G at SEQ ID NO: 19; and/or a C at SEQ ID NO: 22; an A at SEQ ID NO: 23; a T at SEQ ID NO: 25.

Further described is a combination of two isolated nucleic acid molecules, the first nucleic acid molecule encoding a first functional restorer gene allele for wheat G-type cytoplasmic male sterility, wherein said first functional restorer gene allele localises within an interval on wheat chromosome 1A comprising and flanked by the markers of SEQ ID NO 2 and SEQ ID NO 4, and the second isolated nucleic acid molecule encoding a second functional restorer gene allele for wheat G-type cytoplasmic male sterility, wherein said second functional restorer gene allele localises within an interval on wheat chromosome 1B comprising and flanked by the markers of SEQ ID NO 7 and SEQ ID NO 13.

The first functional restorer gene allele can be identifiable using at least one marker allele linked to said functional restorer gene allele for wheat G-type cytoplasmic male sterility located on chromosome 1A, wherein said at least one marker allele localises within an interval on chromosome 1A comprising and flanked by the markers of SEQ ID NO 2 and SEQ ID NO 4 and/or said second functional restorer gene allele can be identifiable using at least one marker allele linked to said functional restorer gene allele for wheat G-type cytoplasmic male sterility located on chromosome 1B, wherein said at least one marker allele localises within an interval on chromosome 1A comprising and flanked by the markers of SEQ ID NO 7 and SEQ ID NO 13.

The first functional restorer gene allele can localize within an interval on chromosome 1A comprising and flanked by the markers of SEQ ID NO. 16 and SEQ ID NO. 19 and/or the second functional restorer gene allele can localize within an interval on chromosome 1B comprising and flanked by the markers of SEQ ID NO: 22 and SEQ ID NO: 25.

The first functional restorer gene allele can be identifiable using at least one marker allele linked to said functional restorer gene allele for wheat G-type cytoplasmic male sterility located on chromosome 1A, wherein said at least one marker allele localises within an interval on chromosome 1A comprising and flanked by the markers of SEQ ID NO. 16 and SEQ ID NO. 19 and/or the second functional restorer gene allele can be identifiable using at least one marker allele linked to said functional restorer gene allele for wheat G-type cytoplasmic male sterility located on chromosome 1A, wherein said at least one marker allele localises within an interval on chromosome 1B comprising and flanked by the markers of SEQ ID NO: 22 and SEQ ID NO: 25.

The first and/or said second functional restorer gene alleles can be obtainable from USDA accession number PI 583676.

Also described is a combination of isolated polypeptides, the first isolated polypeptide being encoded by the first nucleic acid molecule as described herein, the second polypeptide being encoded by the second nucleic acid molecule as described herein.

Also described is a combination of chimeric genes, the first chimeric gene comprising the following operably linked elements
a. a plant-expressible promoter;
b. a nucleic acid comprising the first isolated nucleic acid molecule as described herein or encoding the first isolated polypeptide as described herein; and optionally
c. a transcription termination and polyadenylation region functional in plant cells,
the second chimeric gene comprising the following operably linked elements
d. a plant-expressible promoter;
e. a nucleic acid comprising the second isolated nucleic acid molecule as described herein or encoding the second isolated polypeptide as described herein; and optionally
f. a transcription termination and polyadenylation region functional in plant cells,
wherein in each chimeric gene at least one of said operably linked elements is heterologous with respect to at least one other element.

Further described is a cereal plant cell or cereal plant or seed thereof, such as a wheat plant cell or plant or seed thereof, comprising the first and second isolated nucleic acid molecule as described herein, the first and second isolated polypeptide as described herein, or the first and second chimeric gene as described herein, wherein said isolated polypeptides, said isolated nucleic acids, or said chimeric genes in each case are heterologous with respect to said plant cell or plant or seed.

The plant cell, plant or seed can be a hybrid plant cell, plant or seed.

Further, a method is described for producing a cereal plant cell or plant or seed thereof, such as a wheat plant cell or plant or seed thereof, comprising two functional restorer genes for wheat G-type cytoplasmic male sterility, comprising the steps of providing said plant cell or plant with the combination of isolated nucleic acid molecules as described herein or the combination of chimeric genes as described herein, wherein said providing comprises transformation, crossing, backcrossing, genome editing or mutagenesis.

Further described is the use of the (combination of) isolated nucleic acid molecules as described herein to identify one or more further functional restorer gene alleles for wheat G-type cytoplasmic male sterility.

Further described is the use of at least one marker comprising an allele linked to a functional restorer gene for wheat G-type cytoplasmic male sterility located on chromosome 1A and at least one marker comprising an allele linked to a functional restorer gene for wheat G-type cytoplasmic male sterility located on chromosome 1B as described herein to identify one further marker comprising an allele linked to a functional restorer gene for wheat G-type cytoplasmic male sterility located on chromosome 1A and at least one further marker comprising an allele linked to a functional restorer gene for wheat G-type cytoplasmic male sterility located on chromosome 1B.

Further described is the use of at least one marker comprising an allele linked to a functional restorer gene allele for wheat G-type cytoplasmic male sterility located on chromosome 1A and at least one marker comprising an allele linked to a functional restorer gene allele for wheat G-type cytoplasmic male sterility located on chromosome 1B as described herein for the identification of a plant comprising said functional restorer gene for wheat G-type cytoplasmic male sterility located on chromosome 1A and said functional restorer gene for wheat G-type cytoplasmic male sterility located on chromosome 1B.

Further described is the use of a plant as described herein or obtained by any of the methods as described herein, said plant comprising at least one marker allele linked to said functional restorer gene for wheat G-type cytoplasmic male sterility located on chromosome 1A and at least one marker allele linked to said functional restorer gene for wheat G-type cytoplasmic male sterility located on chromosome 1B as described herein, said plant comprising said functional restorer gene for wheat G-type cytoplasmic male sterility located on chromosome 1A and said functional restorer gene for wheat G-type cytoplasmic male sterility located on chromosome 1B, for restoring fertility in a progeny of a G-type cytoplasmic male sterile cereal plant, such as a wheat plant.

Further described is the use of a plant as described herein or a plant obtained by any of the methods described herein, said plant comprising at least one marker allele linked to said functional restorer gene for wheat G-type cytoplasmic male sterility located on chromosome 1A and at least one marker allele linked to said functional restorer gene for wheat G-type cytoplasmic male sterility located on chromosome 1B as described herein, said plant comprising said functional restorer gene for wheat G-type cytoplasmic male sterility located on chromosome 1A and said functional restorer gene for wheat G-type cytoplasmic male sterility located on chromosome 1B, for producing hybrid seed or a population of hybrid cereal plants, such as hybrid wheat seeds or plants.

FIGURE LEGENDS

FIG. 1: Seed set on the main head (ss_mh), as observed in two different locations (g, m). Number of plants (y-axis) per class of amount of seed (x-axis).

Figure 2:
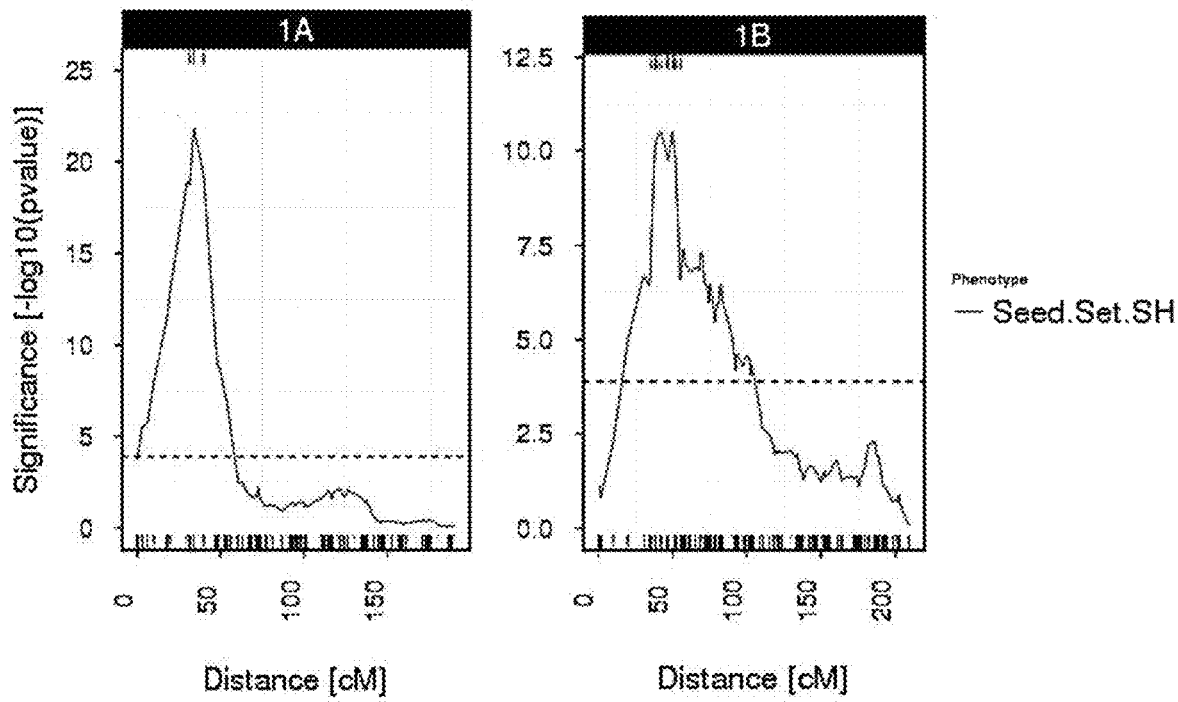

FIG. 2: Profile plot for significance of marker-trait associations along chromosome 1A and 1B in $-\log 10(p)$ Indicative threshold=3.9.

Figure 3:
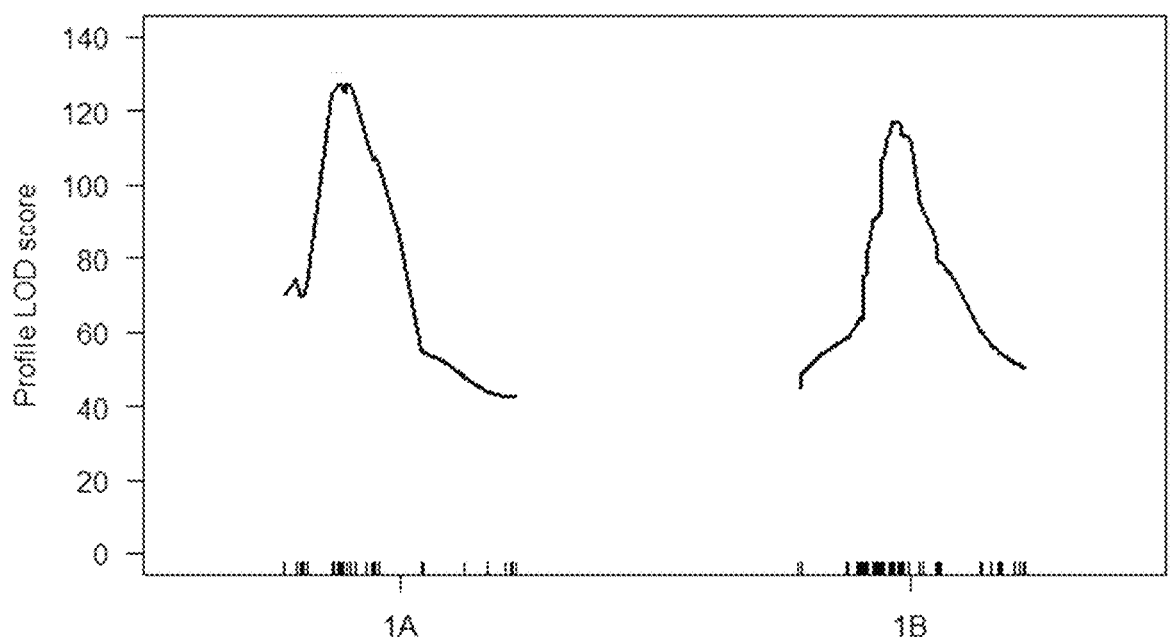

FIG. 3: Significance of marker-trait associations at the F2 generation when assuming a 2-QTL model with an interaction term, as calculated using R-QTL.

Figure 4:
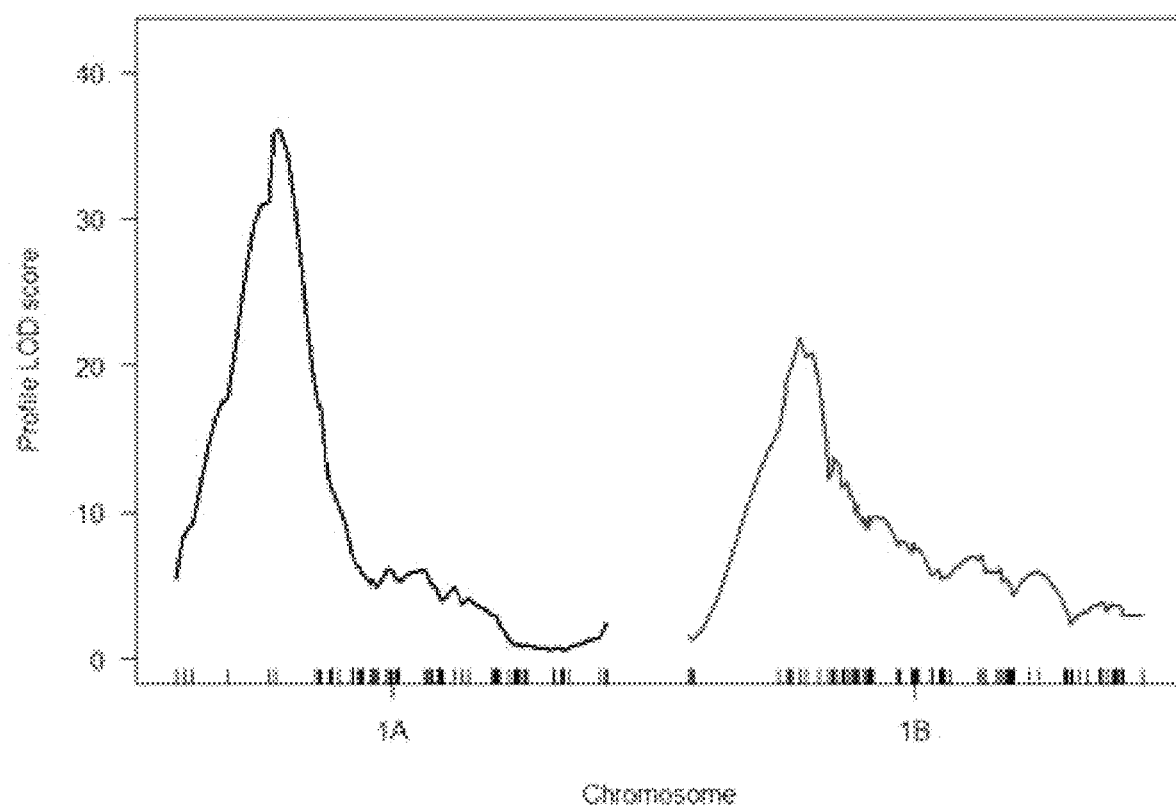

FIG. 4: Significance of marker-trait associations at the F3 generation when assuming a 2-QTL model with an interaction term, as calculated using R-QTL.

Figure 5:
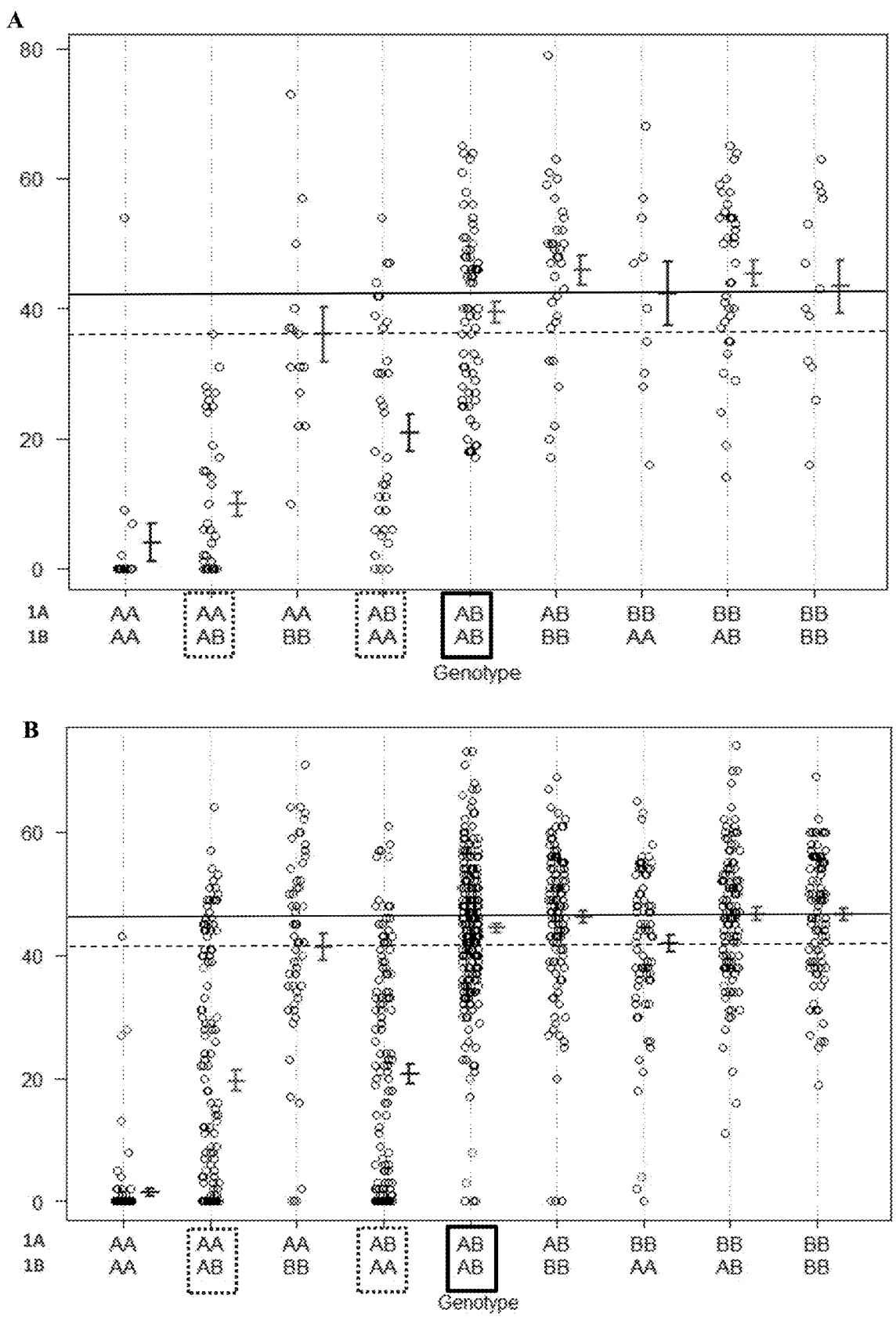

FIG. 5: A: Seed set (seeds/bagged spike) on main head in function of peak marker genotype at 1A and 1B loci in the F2 generation (n=276). Solid boxed—double heterozygous individuals; dashed boxes—single heterozygous individuals. Solid horizontal line—1A, 1A/1B homozygous; dashed horizontal line—1B homozygous. For clarity, AA means homozygous non-Rf, AB means heterozygous non-Rf/Rf, BB means homozygous Rf, in each case for chromosome 1A (upper) and 1B (lower)

B: Seed set (seeds/bagged spike) on main head in function of peak marker genotype at 1A and 1B loci in the F3 generation (n=1096). Solid boxed—double heterozygous individuals; dashed boxes—single heterozygous individuals. Solid horizontal line 1A/1B heterozygous; dashed horizontal line 1A and 1B homozygous. For clarity, AA means homozygous non-Rf, AB means heterozygous non-Rf/Rf, BB means homozygous Rf, in each case for chromosome 1A (upper) and 1B (lower).

DETAILED DESCRIPTION

The present invention describes the identification of a functional restorer (Rf) locus and gene for wheat G-type cytoplasmic male sterility (i.e., *T. timopheevi* cytoplasm) located on chromosome 1A (short arm 1AS), also referred to as Rf1, and on chromosome 1B (short arm 1BS), also referred to as Rf3, as well as markers associated therewith. Said markers can be used in marker-assisted selection (MAS) of cereal plants, such as wheat, comprising said functional restorer genes located on chromosomes 1A and 1B. The identification of the genes and markers are therefore extremely useful in methods for hybrid seed production, as they can be used e.g. in a method for restoring fertility in progeny of a plant possessing G-type cytoplasmic male sterility, thereby producing fertile progeny plants from a G-type cytoplasmic male sterile parent plant. Likewise, the present disclosure also allows identifying plants lacking the desired allele, so that non-restorer plants can be identified and, e.g., eliminated from subsequent crosses.

One advantage of marker-assisted selection over field evaluations for fertility restoration is that MAS can be done at any time of year regardless of the growing season. Moreover, environmental effects are irrelevant to marker-assisted selection.

When a population is segregating for multiple loci affecting one or multiple traits, e.g., multiple loci involved in fertility restoration or multiple loci each involved in fertility restoration of different cytoplasmic male sterility (CMS) systems or loci affecting distinct traits (for example fertility and disease resistance) the efficiency of MAS compared to phenotypic screening becomes even greater because all the loci can be processed in the lab together from a single sample of DNA. Any one or more of the markers and/or marker alleles, e.g., two or more, up to and including all of the established markers, can be assayed simultaneously.

Another use of MAS in plant breeding is to assist the recovery of the recurrent parent genotype by backcross breeding. Backcross breeding is the process of crossing a progeny back to one of its parents. Backcrossing is usually done for the purpose of introgressing one or a few loci from a donor parent into an otherwise desirable genetic background from the recurrent parent. The more cycles of backcrossing that are done, the greater the genetic contribution of the recurrent parent to the resulting variety. This is often necessary, because donor parent plants may be otherwise undesirable, i.e., due to low yield, low fecundity or the like. In contrast, varieties which are the result of intensive breeding programs may have excellent yield, fecundity or the like, merely being deficient in one desired trait such as fertility restoration. As a skilled worker understands, backcrossing can be done to select for or against a trait. For example, in the present invention, one can select a restorer gene for breeding a restorer line or one select against a restorer gene for breeding a maintainer (female pool).

In particular, it was surprisingly found that when combining the functional restorer loci located on chromosome 1A and 1B when restoring fertility in offspring of a G-type cytoplasmic male sterile wheat plant, an improved restoration capacity was observed when compared to using either one of the 1A or 1B loci, indicating an epistasis between the two loci. Accordingly, the markers specific for the 1A and the 1B locus can be used together to identify plants comprising both loci, for use in a method for improved fertility restoration.

The presently described Rf locus on chromosome 1A was mapped to a segment along the chromosome 1A, in an interval of about 15.6 cM, said interval being flanked by markers as represented by SEQ ID NO 2 and SEQ ID NO 4.

The presently described Rf locus on chromosome 1B was mapped to a segment along the chromosome 1B, in an interval of about 15.8 cM, said interval being flanked by markers of SEQ ID NO 7 and SEQ ID NO 13.

Thus, in a first aspect, a method is provided for selecting a cereal plant comprising at least two functional restorer gene allele(s) (i.e. a functional allele for each of at least two restorer genes) for wheat G-type cytoplasmic male sterility or for producing a cereal plant comprising at least two functional restorer gene alleles (i.e. a functional allele for each of at least two restorer genes) for wheat G-type cytoplasmic male sterility, comprising the steps of:

(a) identifying at least one cereal plant comprising at least one marker allele linked to a functional restorer gene allele for wheat G-type cytoplasmic male sterility located on chromosome 1A (1A restorer marker allele) and comprising at least one marker allele linked to a functional restorer gene allele for wheat G-type cytoplasmic male sterility located on chromosome 1B (1B restorer marker allele); and (b) selecting the plant comprising said at least one 1A restorer marker allele and said at least one 1B restorer marker allele, wherein said plant comprises said functional restorer gene for wheat G-type cytoplasmic male sterility located on chromosome 1A (1A restorer gene allele) and said functional restorer gene allele for wheat G-type cytoplasmic male sterility located on chromosome 1B (1B restorer gene allele)

wherein said at least one 1A restorer marker allele localises within an interval on chromosome 1A comprising and flanked by the markers of SEQ ID NO 2 and SEQ ID NO 4 and wherein said at least one 1B localises within an interval on chromosome 1B comprising and flanked by the markers of SEQ ID NO 7 and SEQ ID NO 13.

Thus, by selecting or producing a plant with said two functional restorer gene alleles (i.e. one on chromosome 1A and one on chromosome 1B) as described, a plant is selected or produced that has improved fertility restoration capacity against wheat G-type cytoplasmic male sterility, than a plant having only one of said two functional restorer gene alleles on either one of 1A or 1B.

In a second aspect, a method is provided for restoring fertility in a progeny of a G-type cytoplasmic male sterile cereal plant or for producing a fertile progeny plant from a G-type cytoplasmic male sterile cereal parent plant, comprising the steps of (a) Providing a population of progeny plants obtained from crossing a female cereal parent plant with a male cereal parent plant, wherein the female parent plant is a G-type cytoplasmic male sterile cereal plant, and wherein the male parent plant comprises a functional restorer gene allele for wheat G-type cytoplasmic male sterility located on chromosome 1A (1A restorer gene allele) and a functional restorer gene allele for wheat G-type cytoplasmic male sterility located on chromosome 1B (1B restore gene allele);

(b) Identifying in said population a fertile progeny plant comprising at least one marker allele linked to said functional restorer gene allele for wheat G-type cytoplasmic male sterility located on chromosome 1A (1A restorer marker allele) and at least one marker allele linked to said functional restorer gene allele for wheat G-type cytoplasmic male sterility located on chromosome 1B (1B restorer marker allele), wherein said progeny plant comprises said functional 1A restorer gene allele and said functional 1B restorer gene allele; optionally
(c) Selecting said fertile progeny plant; and optionally
(d) Propagating the fertile progeny plant,
wherein said at least one 1A restorer marker allele localises within an interval on chromosome 1A comprising and flanked by the markers of SEQ ID NO 2 and SEQ ID NO 4 and wherein said at least one 1B localises within an interval on chromosome 1B comprising and flanked by the markers of SEQ ID NO 7 and SEQ ID NO 13.

Thus, by using a male parent plant comprising both the 1A and 1B functional restorer gene alleles, as can be determined by the presence of the herein disclosed 1A and 1B restorer marker alleles, an improved fertility restoration can be achieved against wheat G-type cytoplasmic male sterility than when using a plant having only on of said functional restorer gene alleles on either 1A or 1B.

Male sterility in connection with the present invention refers to the failure or partial failure of plants to produce functional pollen or male gametes. This can be due to natural or artificially introduced genetic predispositions or to human intervention on the plant in the field. Male fertile on the other hand relates to plants capable of producing normal functional pollen and male gametes. Male sterility/fertility can be reflected in seed set upon selfing, e.g. by bagging heads to induce self-fertilization. Likewise, fertility restoration can also be described in terms of seed set upon crossing a male sterile plant with a plant carrying a functional restorer gene, when compared to seed set resulting from crossing (or selfing) fully fertile plants.

A male parent or pollen parent, is a parent plant that provides the male gametes (pollen) for fertilization, while a female parent or seed parent is the plant that provides the female gametes for fertilization, said female plant being the one bearing the seeds.

Cytoplasmic male sterility or "CMS" refers to cytoplasmic-based and maternally-inherited male sterility. CMS is total or partial male sterility in plants as the result of specific nuclear and mitochondrial interactions and is maternally inherited via the cytoplasm. Male sterility is the failure of plants to produce functional anthers, pollen, or male gametes although CMS plants still produce viable female gametes. Cytoplasmic male sterility is used in agriculture to facilitate the production of hybrid seed.

"Wheat G-type cytoplasmic male sterility", as used herein refers to the cytoplasm of *Triticum* timopheevi that can confer male sterility when introduced into common wheat (i.e. *Triticum aestivum*), thereby resulting in a plant carrying common wheat nuclear genes but cytoplasm from *Triticum timopheevii* that is male sterile. The cytoplasm of *Triticum* timopheevi (G-type) as inducers of male sterility in common wheat have been extensively studied (Wilson and Ross, Genes Genet. Syst. 1962; Kaul, Male sterility in higher plants. Springer Verlag, Berlin. 1988; Lucken, Hybrid wheat. In Wheat and wheat improvement. Edited by E. G. Heyne. American Society of Agronomy, Madison, Wis., 1987; Mukai and Tsunewaki, Theor. Appl. Genet. 54, 1979; Tsunewaki, Jpn. Soc. Prom. Sci. 1980; Tsunewaki et al., Genes Genet. Syst. 71, 1996). The origin of the CMS phenotype conferred by *T. timopheevi* cytoplasm is with a novel chimeric gene termed orf256, which is upstream of cox1 sequences and is cotranscribed with an apparently normal cox1 gene. Antisera prepared against polypeptide sequences predicted from orf256 recognized a 7-kDa protein present in the CMS line but not in the parental or restored lines (Song and Hedgcoth, Genome 37(2), 1994; Hedgcoth et al., Curr. Genet. 41, 357-365, 2002).

As used herein "a functional restorer gene allele for wheat G-type cytoplasmic male sterility" or "a functional restorer locus for wheat G-type cytoplasmic male sterility" or a "restorer QTL for wheat G-type cytoplasmic male sterility" indicates an allele that has the capacity to restore fertility in the progeny of a cross with a G-type cytoplasmic male sterility ("CMS") line, i.e., a line carrying common wheat nuclear genes but cytoplasm from *Triticum timopheevii*. Restoration against G-type cytoplasm has e.g. been described by Robertson and Curtis (Crop Sci. 9, 1967), Yen et al. (Can. J. Genet. Cytol. 11, 1969), Bahl and Maan (Crop Sci. 13, 1973), Talaat et al. (Egypt. J. Genet. 2, 195-205, 1973) Zhang et al., (2003, supra) Ma and Sorrels (1995, supra), Kojima (1997, supra), Ahmed Talaat et al (2001, supra), Zhou et al (2005, supra). Such restorer genes or alleles are also referred to as Rf genes and Rf alleles.

The term "maintainer" refers to a plant that when crossed with the CMS plant does not restore fertility, and maintains sterility in the progeny. The maintainer is used to propagate the CMS line, and may also be referred to as a non-restorer line. Maintainer lines have the same nuclear genes as the sterile one (i.e. do not contain functional Rf genes), but differ in the composition of cytoplasmic factors that cause male sterility in plants i.e. maintainers have "fertile" cytoplasm. Therefore when a male sterile line is crossed with its maintainer progeny with the same male sterile genotype will be obtained.

The term "cereal" relates to members of the monocotyledonous family Poaceae which are cultivated for the edible components of their grain. These grains are composed of endosperm, germ and bran. Maize, wheat and rice together account for more than 80% of the worldwide grain production. Other members of the cereal family comprise rye, oats, barley, triticale, sorghum, wild rice, spelt, einkorn, emmer, durum wheat and kamut.

In one embodiment, a cereal plant according to the invention is a cereal plant that comprises at least an A and a B or related genomes, such as wheat (*Triticum aestivum*; ABD), spelt (*Triticum spelta*; ABD) durum (*T. turgidum*; AB), barley (*Hordeum vulgare*; H) and rye (*Secale cereale*; R). In a specific embodiment, the cereal plant according to the invention is wheat (*Triticum aestivum*; ABD).

A "molecular marker" or "marker" or "marker nucleic acid" or "genetic marker", as used herein, refers to a polymorphic locus, i.e. a polymorphic nucleotide (a so-called single nucleotide polymorphism or SNP) or a polymorphic DNA sequence at a specific locus. A marker refers to a measurable, genetic characteristic with a fixed position in the genome, which is normally inherited in a Mendelian fashion, and which can be used for mapping of a trait of interest or to identify certain individuals with a certain trait of interest. A marker thus refers to a gene or nucleotide sequence that can be used to identify plants having a particular allele, e.g., the presently described Rf alleles on chromosome 1A and 1B. A marker may be described as a variation at a given genomic locus. It may be a short DNA sequence, such as a sequence surrounding a single base-pair change (single nucleotide polymorphism, or "SNP"), or a long one, for example, a microsatellite/simple sequence repeat ("SSR"). A molecular marker may also include 'Indels' which refers to the insertion or the deletion of bases or a combination of both in the DNA of an organism, and which can be used as molecular markers.

The term "marker genotype" refers to the combination of marker alleles present at a polymorphic locus on each chromosome of the chromosome pair. The term "marker allele" refers to the version of the marker that is present in a particular plant at one of the chromosomes. Typically, a marker can exist as or can be said to have or to comprise two marker alleles. The term "haplotype", as used herein, refers to a specific combination of marker alleles as present within a certain plant or group of (related) plants. See also the below definitions of a SNP (marker) genotype and SNP (marker) allele.

A "marker context" or "marker context sequence", as used herein, refers to 50-150 bp upstream of a marker, such as a SNP marker, and/or 50-150 bp downstream of such a marker. The marker context of the herein described (SNP) markers is given in the sequence listing, flanking the SNP position. The upstream and downstream sequences of a (SNP) marker can also be referred to as (upstream and/or downstream) flanking sequences.

Identifying a cereal plant comprising at least one marker allele linked to a functional restorer gene allele for wheat G-type cytoplasmic male sterility located on chromosome 1A and at least one marker allele linked to a functional restorer gene allele for wheat G-type cytoplasmic male sterility located on chromosome 1B can be accomplished using a molecular marker assay that detects the presence of at least one such marker alleles on each chromosome, e.g. the marker alleles described herein that are linked to the functional restorer gene allele for wheat G-type cytoplasmic male sterility located on chromosome 1A and 1B. This can involve obtaining or providing a biological sample, i.e. plant material, or providing genomic DNA of a plant, and analyzing the genomic DNA of the material for the presence of at least one of said marker alleles (or for the marker genotype for at least one of such markers). In this method also other molecular marker tests described elsewhere herein can be used.

As will be well known to a person skilled in the art, markers and marker assays include for example Restriction Fragment Length Polymorphisms (RFLPs), Random Amplified Polymorphic DNA's (RAPDs), Amplified Fragment Length Polymorphism's (AFLPs), DAF, Sequence Characterized Amplified Regions (SCARs), microsatellite or Simple Sequence Repeat markers (SSRs), Sequence Characterized Amplified Regions (SCARs), single-nucleotide polymorphisms (SNPs), KBioscience Competitive Allele-Specific PCR (KASPar), as inter alia described in Jonah et al. (Global Journal of Science Frontier Research 11:5, 2011) and Lateef (Journal of Biosciences and Medicines, 2015, 3, 7-18).

As used herein, the term "single nucleotide polymorphism" (SNP) may refer to a DNA sequence variation occurring when a single nucleotide in the genome (or other shared sequence) differs between members of a species or paired chromosomes in an individual. Within a population, SNPs can be assigned a minor allele frequency the lowest allele frequency at a locus that is observed in a particular population. This is simply the lesser of the two allele frequencies for single-nucleotide polymorphisms. There are variations between various populations, so a SNP allele that is common in one geographical group or variety may be much rarer in another.

Single nucleotide polymorphisms may fall within coding sequences of genes, non-coding regions of genes, or in the intergenic regions between genes. SNPs within a coding sequence will not necessarily change the amino acid sequence of the protein that is produced, due to degeneracy of the genetic code. A SNP in which both forms lead to the same polypeptide sequence is termed "synonymous" (sometimes referred to a silent mutation). If a different polypeptide sequence is produced, they are termed "non-synonymous." A non-synonymous change may either be mis-sense or nonsense, where a mis-sense change results in a different amino acid and a nonsense change results in a premature stop codon. SNPs that are not in protein-coding regions may still have consequences for e.e. gene splicing, transcription factor binding, or the sequence of non-coding RNA (e.g. affecting transcript stability, translation). SNPs are usually biallelic and thus easily assayed in plants and animals.

A particularly useful assays for detection of SNP markers is for example KBioscience Competitive Allele-Specific PCR (KASP, see world wide web at kpbioscience.co.uk, For developing the KASP-assay 70 base pairs upstream and 70 basepairs downstream of the SNP are selected and two allele-specific forward primers and one allele specific reverse primer is designed. See e.g. Allen et al. 2011, Plant Biotechnology J. 9, 1086-1099, especially p1097-1098 for KASP assay method.

The terms "linked to" or "linkage", as used herein, refers to a measurable probability that genes or markers located on a given chromosome are being passed on together to individuals in the next generation. Thus, the term "linked" may refer to one or more genes or markers that are passed together with a gene with a probability greater than 0.5 (which is expected from independent assortment where markers/genes are located on different chromosomes). Because the proximity of two genes or markers on a chromosome is directly related to the probability that the genes or markers will be passed together to individuals in the next generation, the term "linked" may also refer herein to one or more genes or markers that are located within about 50 centimorgan (cM) or less of one another on the same chromosome. Genetic linkage is usually expressed in terms of cM. Centimorgan is a unit of recombinant frequency for measuring genetic linkage, defined as that distance between genes or markers for which one product of meiosis in 100 is recombinant, or in other words, the centimorgan is equal to a 1% chance that a marker at one genetic locus on a chromosome will be separated from a marker at a second locus due to crossing over in a single generation. It is often used to infer distance along a chromosome. The number of base-pairs to which cM correspond varies widely across the genome (different regions of a chromosome have different propensities towards crossover) and the species (i.e. the total size of the genome).

The presently described Rf locus on chromosome 1A was mapped to a segment at chromosome 1A, in an interval of about 15.6 cM, said interval being flanked by markers of SEQ ID NO 2 and SEQ ID NO. 4. These and any marker located in between can be said to comprise an allele that is linked to functional restorer gene for wheat G-type cytoplasmic male sterility located on chromosome 1A. The peak marker was the marker of SEQ ID NO. 3. Particular examples of markers comprising an allele linked to the functional restorer gene for wheat G-type cytoplasmic male sterility located on chromosome 1A are specified in table 1A.

The presently described Rf locus on chromosome 1B was mapped to a segment at chromosome 1B, in an interval of about 15.8 cM, said interval being flanked by markers of SEQ ID NO 7 and SEQ ID NO. 13. These and any marker located in between can be said to comprise an allele that is linked to functional restorer gene for wheat G-type cytoplasmic male sterility located on chromosome 1B. The peak marker was the marker of SEQ ID NO. 11. Particular examples of markers comprising an allele linked to the functional restorer gene for wheat G-type cytoplasmic male sterility located on chromosome 1B are specified in table 1B.

Thus, in this respect, the term linked can be a separation of about 15.8 cM or of about 15.6 cM, or less such as about 15 cM, about 12.5 cM, about 10 cM, 7.5 cM, about 6 cM, about 5 cM, about 4 cM, about 3 cM, about 2.5 cM, about 2 cM, or even less.

Further finemapping narrowed the 1A region to an interval of about 1.9 cM (from 30.9 to 32.8 cM), comprising the markers as represented by SEQ ID NO. 16, SEQ ID NO. 17, SEQ ID NO. 18 and SEQ ID NO. 19. These and any further marker located in said interval can be said to comprise an allele that is "tightly linked" to the functional restorer gene for wheat G-type cytoplasmic male sterility located on chromosome 1A. The marker closest to the peak was SEQ ID NO. 18. Particular examples of markers or marker alleles tightly linked to the functional restorer gene for wheat G-type cytoplasmic male sterility located on chromosome 1A are given in table 2B.

Further finemapping narrowed the 1B region to an interval of about 1.25 cM (from 6.8 to 8.05 cM), comprising the markers as represented by SEQ ID NO. 22, SEQ ID NO. 23, SEQ ID NO. 24 and SEQ ID NO. 25. These and any further marker located in said interval can be said to comprise an allele that is "tightly linked" to the functional restorer gene for wheat G-type cytoplasmic male sterility located on chromosome 1B. The marker closest to the peak was SEQ ID NO. 24. Particular examples of markers or marker alleles tightly linked to the functional restorer gene for wheat G-type cytoplasmic male sterility located on chromosome 1B are given in table 2B.

Thus, the term "tightly linked" as used herein can be a separation of about 1.9 cM, or even less, such as about 1.55 cM, about 1.5 cM, about 1.25 cM about, 1.0 cM, about 0.95 cM, about 0.9 cM, about 0.85 cM, about 0.8 cM, about 0.75 cM, about 0.5 cM, about 0.4 cM, about 0.3 cM about 0.25 cM, about 0.20 cM, about 0.15 cM, about 0.10 cM, or even less.

Thus, said at least one marker allele linked to said functional restorer gene allele located on chromosome 1A (1A restorer marker allele) can be selected from any one of:
 a. an A at SEQ ID NO: 2;
 b. a C at SEQ ID NO: 3;
 c. a C at SEQ ID NO: 4;
 d. a C at SEQ ID NO: 16;
 e. a G at SEQ ID NO: 17;
 f. a C at SEQ ID NO: 18;
 g. a G at SEQ ID NO: 19,
or any combination thereof.

Thus, said at least one marker allele linked to said functional restorer gene allele located on chromosome 1B (1B restorer marker allele) can be selected from any one of:
 a. a T at SEQ ID NO: 7;
 b. a C at SEQ ID NO: 8;
 c. a T at SEQ ID NO: 9;
 d. a T at SEQ ID NO: 10;
 e. an A at SEQ ID NO: 11;
 f. an A at SEQ ID NO: 12;
 g. a G at SEQ ID NO: 13;
 h. a C at SEQ ID NO: 22;
 l. an A at SEQ ID NO: 23,
 j. a T at SEQ ID NO: 24;
 k. a T at SEQ ID NO: 25,
or any combination thereof.

As used herein, "an A at SEQ ID NO: 2" or "a C at SEQ ID NO. 3" and the like, refers to an A or a C etc being present at a position corresponding to the position of the SNP in said SEQ ID NO, as e.g. indicated in table 1 or 2. This can for example be determined by alignment of the genomic sequence with said SEQ ID NO. Thus, "an A at SEQ ID NO: 2" means "an A at a position corresponding to position 51 of SEQ ID NO: 2", etc.

In a further embodiment, said at least one 1A restorer marker allele localises to an interval from 30.9 to 32.8 cM on chromosome 1A. Said 1.9 cM interval comprises the markers of SEQ ID NO. 16, SEQ ID. NO. 17, SEQ ID NO. 18 and SEQ ID NO. 19 at the map positions as indicated in table 2A.

For example, said at least one marker allele linked to said functional restorer gene allele located on chromosome 1A can be selected from any one of:
 a. a C at SEQ ID NO: 16;
 b. a G at SEQ ID NO: 17;
 c. a C at SEQ ID NO: 18;
 d. a G at SEQ ID NO: 19,
or any combination thereof.

In a further embodiment, said at least one 1B restorer marker allele localises to an interval from 30.9 to 32.8 cM on chromosome 1B. Said 1.25 cM interval comprises the markers of SEQ ID NO. 11, SEQ ID. NO. 12, SEQ ID NO. 13 and SEQ ID NO. 14 at the map positions as indicated in table 2B.

For example, said said at least one marker allele linked to said functional restorer gene allele located on chromosome 1B can be selected from any one of:
 a. a C at SEQ ID NO: 22;
 b. an A at SEQ ID NO: 23,
 c. a T at SEQ ID NO: 24;
 d. a T at SEQ ID NO: 25,
or any combination thereof.

In an even further embodiment, said at least one marker allele linked to said functional restorer gene for wheat G-type cytoplasmic male sterility located on chromosome 1A localises to an interval of 1.55 cM (from 31.25 to 32.8 cM) on chromosome 1A flanked by and comprising the marker pair of SEQ ID NO. 16 and SEQ ID NO. 19.

In an even further embodiment, said at least one marker allele linked to said functional restorer gene for wheat G-type cytoplasmic male sterility located on chromosome 1B localises to an interval of 0.95 cM (from 7.1 to 8.05 cM) on chromosome 1B flanked by and comprising the marker pair of SEQ ID NO. 22 and SEQ ID NO. 25.

In a particular embodiment, said at least one marker allele linked to said functional restorer gene allele located on chromosome 1A is a C at SEQ ID NO. 18.

In a particular embodiment, said at least one marker allele linked to said functional restorer gene allele located on chromosome 1B is a T at SEQ ID NO. 24.

The term "interval" refers to a continuous linear span of chromosomal DNA with termini defined by map position and/or markers. For example, the interval comprising and flanked by the marker pair of SEQ ID NO: 16 and SEQ ID NO: 19 comprises the specifically mentioned flanking markers and the markers located in between, e.g. SEQ ID NO. 17 and 18 as listed in the table 2A below, while the interval comprising and flanked by the marker pair of SEQ ID NO: 22 and SEQ ID NO: 25 comprises the specifically mentioned flanking markers and the markers located in between, e.g. SEQ ID NO. 23 and 24 as listed in table 2 below. The interval comprising and flanked by the marker pair of SEQ ID NO. 2 and SEQ ID NO. 4 comprises the markers of SEQ ID NO. 3 as well as the markers of SEQ ID NO. 16-19, while the interval comprising and flanked by the marker pair of SEQ ID NO. 7 and SEQ ID NO. 13 comprises the markers of SEQ ID NO. 8-12, as well as the markers of SEQ ID NO. 22-25. Accordingly, a flanking marker as used herein, is a marker that defines one of the termini of an interval (and is included in that interval). It will be clear that any of such intervals may comprise further markers not specifically mentioned herein.

The position of the chromosomal segments identified, and the markers thereof, when expressed as recombination frequencies or map units, are provided herein as a matter of general information. The embodiments described herein were obtained using particular wheat populations. Accordingly, the positions of particular segments and markers as map units are expressed with reference to the used populations. It is expected that numbers given for particular segments and markers as map units may vary from cultivar to cultivar and are not part of the essential definition of the DNA segments and markers, which DNA segments and markers are otherwise described, for example, by nucleotide sequence.

A locus (plural loci), as used herein refers to a certain place or position on the genome, e.g. on a chromosome or chromosome arm, where for example a gene or genetic marker is found. A QTL (quantitative trait locus), as used herein, and refers to a position on the genome that corresponds to a measurable characteristic, i.e. a trait, such as the presently described Rf loci.

As used herein, the term "allele(s)" of a gene means any of one or more alternative forms of a gene at a particular locus. In a diploid cell of an organism, alleles of a given gene are located at a specific location or locus (loci plural) on a chromosome. One allele is present on each chromosome of the pair of homologous chromosomes or possibly on homeologous chromosomes.

As used herein, the term "homologous chromosomes" means chromosomes that contain information for the same biological features and contain the same genes at the same loci but possibly different alleles of those genes. Homologous chromosomes are chromosomes that pair during meiosis. "Non-homologous chromosomes", representing all the biological features of an organism, form a set, and the number of sets in a cell is called ploidy. Diploid organisms contain two sets of non-homologous chromosomes, wherein each homologous chromosome is inherited from a different parent. In tetraploid species, two sets of diploid genomes exist, whereby the chromosomes of the two genomes are referred to as "homeologous chromosomes" (and similarly, the loci or genes of the two genomes are referred to as homeologous loci or genes). Likewise, hexaploid species have three sets of diploid genomes, etc. A diploid, tetraploid or hexaploid plant species may comprise a large number of different alleles at a particular locus. The ploidy levels of domesticated wheat species range from diploid (*Triticum monococcum*, 2n=14, AA), tetraploid (*T. turgidum*, 2n=28, AABB) to hexaploid (*T. aestivum*, 2n=42, AABBDD).

As used herein, the term "heterozygous" means a genetic condition existing when two different alleles reside at a specific locus, but are positioned individually on corresponding pairs of homologous chromosomes in the cell. Conversely, as used herein, the term "homozygous" means a genetic condition existing when two identical alleles reside at a specific locus, but are positioned individually on corresponding pairs of homologous chromosomes in the cell.

An allele of a particular gene or locus can have a particular penetrance, i.e. it can be dominant, partially dominant, co-dominant, partially recessive or recessive. A dominant allele is a variant of a particular locus or gene that when present in heterozygous form in an organism results in the same phenotype as when present in homozygous form. A recessive allele on the other hand is a variant of an allele that in heterozygous form is overruled by the dominant allele thus resulting in the phenotype conferred by the dominant allele, while only in homozygous form leads to the recessive phenotype. Partially dominant, co-dominant or partially recessive refers to the situation where the heterozygote displays a phenotype that is an intermediate between the phenotype of an organism homozygous for the one allele and an organism homozygous for the other allele of a particular locus or gene. This intermediate phenotype is a demonstration of partial or incomplete dominance or penetrance. When partial dominance occurs, a range of phenotypes is usually observed among the offspring. The same applies to partially recessive alleles.

Cytoplasmic male-sterility is caused by one or more mutations in the mitochondrial genome (termed "sterile cytoplasm") and is inherited as a dominant, maternally transmitted trait. For cytoplasmic male sterility to be used in hybrid seed production, the seed parent must contain a sterile cytoplasm and the pollen parent must contain (nuclear) restorer genes (Rf genes) to restore the fertility of the hybrid plants grown from the hybrid seed. Accordingly, also such Rf genes preferably are at least partially dominant, most preferably dominant, in order to have sufficient restoring ability in offspring. It was surprisingly shown herein, that by combining the 1A restorer allele and the 1B restorer allele both in heterozygous form, the restoring effect was much higher than when either one of the alleles was present in heterozygous form, and was about the same level as in single homozygotes.

A chromosomal interval flanked by the above mentioned markers, are for example the markers as listed in Table 1-2 below between the specifically mentioned markers, or other markers that are not explicitly shown, but which are also flanked by the marker pairs mentioned. The skilled person can easily identify new markers in the genomic region or subgenomic region being flanked by any of the marker pairs listed above. Such markers need not to be SNP markers, but can be any type of genotypic or phenotypic marker mapped to that genomic or subgenomic region. Preferably such markers are genetically and physically linked to the presently described Rf loci as present in (and as derivable from) at least Accession number PI 583676 (USDA National Small Grains Collection), but preferably also as present in other cereals comprising the Rf 1A and 1B locus. In other words, the markers are preferably indicative of the presence of the Rf loci in a non-source specific manner.

In a further embodiment, at least two, three, four, or more marker alleles linked to said functional restorer gene for wheat G-type cytoplasmic male sterility located on chromosome 1A can be used, such as, at least two, three, four, or more marker nucleic acids selected from any one of SEQ ID NO. 2, SEQ ID NO. 3, SEQ ID NO. 4, SEQ ID NO. 16, SEQ ID NO. 17, SEQ ID NO. 18, SEQ ID NO. 19.

In a further embodiment, at least two, three, four, or more marker alleles linked to said functional restorer gene for wheat G-type cytoplasmic male sterility located on chromosome 1B can be used, such as, at least two, three, four, or more marker nucleic acids selected from any one of SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 22, SEQ ID NO. 23, SEQ ID NO. 24, SEQ ID NO. 25.

In a further embodiment, at least two, three, four, or more contiguous marker alleles linked to said functional restorer gene for wheat G-type cytoplasmic male sterility located on chromosome 1A may be used. A contiguous marker, as used herein is a nucleotide sequence located "upstream" or "downstream" of another marker, depending on whether the contiguous nucleotide sequence from the chromosome is on the 5' or the 3' side of the original marker, as conventionally understood, e.g. in the order as listed in table 1A or 2A.

In a further embodiment, at least two, three, four, or more contiguous marker alleles linked to said functional restorer gene for wheat G-type cytoplasmic male sterility located on chromosome 1B may be used. A contiguous marker, as used herein is a nucleotide sequence located "upstream" or "downstream" of another marker, depending on whether the contiguous nucleotide sequence from the chromosome is on the 5' or the 3' side of the original marker, as conventionally understood, e.g. in the order as listed in table 1B or 2B.

A "contig", as used herein refers to set of overlapping DNA segments that together represent a consensus region of DNA. In bottom-up sequencing projects, a contig refers to overlapping sequence data (reads); in top-down sequencing projects, contig refers to the overlapping clones that form a physical map of the genome that is used to guide sequencing and assembly. Contigs can thus refer both to overlapping DNA sequence and to overlapping physical segments (fragments) contained in clones depending on the context.

A "scaffold" as, used herein, refers to overlapping DNA contigs that together represent a consensus region of DNA.

In a further embodiment, said functional restorer gene allele is a functional restorer gene allele as present in (and as derivable from) at least Accession number PI 583676 (USDA National Small Grains Collection, also known as Dekalb 582M and registered as US PVP 7400045).

It will be clear that when reference herein is made to a certain SNP genotype or SNP allele (or marker genotype or marker allele) in a specific genomic sequence (selected e.g. from SEQ ID NO: 1 to SEQ ID NO: 25), this encompasses also the SNP genotype or allele in variants of the genomic sequence, i.e. the SNP genotype or allele in a genomic sequence that is homologous, e.g. comprising at least 85%, 90%, 95%, 98%, 99% (substantial) sequence identity or more to the sequence referred to (selected e.g. from SEQ ID NO: 1 to SEQ ID NO: 25). Thus any reference herein to any one of SEQ ID NO: 1 to 25 in one aspect also encompasses a variant (homologous sequence) of any one of SEQ ID NO: 1 to 25, said variant comprising at least 85%, 90%, 95%, 98%, 99% sequence identity or more to said sequence (using e.g. the program 'Needle'), but comprising said SNP (marker) genotype or allele.

The SNP genotype refers to two nucleotides, and genomic sequences comprising one of these two nucleotides, one on each chromosome of the chromosome pair. So a plant having e.g. a CC genotype for has an identical nucleotide (C) on both chromosomes at the position corresponding to nucleotide 51 of SEQ ID NO:3, while a plant having a CT genotype has one chromosome with a C at the position corresponding to nucleotide 51 of SEQ ID NO: 3 and one chromosome with a T at said nucleotide position. Likewise, a plant having e.g. a AA genotype for SEQ ID NO. 11 has an identical nucleotide (A) on both chromosomes at the position corresponding to nucleotide 32 of SEQ ID NO: 11, while a plant having an AG genotype for SEQ ID NO. 11 has one chromosome with an A at the position corresponding to nucleotide 32 of SEQ ID NO: 11 and one chromosome with a G at said nucleotide position. Accordingly, a SNP allele refers to one of the two nucleotides of the SNP genotype as present on a chromosomes.

Based on the present disclosure, the skilled person can easily identify any further Rf specific marker or marker alleles for each chromosomal locus as listed above. This can for example be done by sequencing genomic regions in-between any of the markers mentioned herein or by mapping new markers to a region in between any of the marker intervals or sub-intervals listed above. Preferably, but not necessarily, such markers are common markers, i.e. they are present on chromosome 1A or on chromosome 1B of more than one Rf source.

The invention further describes a method for producing a cereal (e.g. wheat) plant comprising a functional restorer gene allele for wheat G-type cytoplasmic male sterility located in chromosome 1A and a functional restorer gene allele for wheat G-type cytoplasmic male sterility located in chromosome 1B, comprising the steps of a. crossing a first cereal plant comprising a functional restorer gene for wheat G-type cytoplasmic male sterility located on chromosome 1A and a functional restorer gene allele for wheat G-type cytoplasmic male sterility located in chromosome 1B, with a second plant (wherein said first cereal plant comprises at least one marker allele linked to a functional restorer gene allele for wheat G-type cytoplasmic male sterility located on chromosome 1A as described herein and at least one marker allele linked to a functional restorer gene allele for wheat G-type cytoplasmic male sterility located on chromosome 1B as described herein, and hence is identifiable using the methods described herein)

b. identifying (and optionally selecting) a progeny plant comprising a functional restorer gene allele for wheat G-type cytoplasmic male sterility located on chromosome 1A and comprising a functional restorer gene allele for wheat G-type cytoplasmic male sterility located on chromosome 1B according to any of the methods described herein, by identifying a progeny plant comprising at least one marker allele linked to said functional restorer gene allele for wheat G-type cytoplasmic male sterility located on chromosome 1A and at least one marker allele linked to said functional restorer gene allele for wheat G-type cytoplasmic male sterility located on chromosome 1B as described herein (wherein said progeny plant comprises said functional restorer gene for wheat G-type cytoplasmic male sterility located on chromosome 1A and said functional restorer gene for wheat G-type cytoplasmic male sterility located on chromosome 1B).

Also provided is a method for producing a cereal plant comprising a functional restorer gene allele for wheat G-type cytoplasmic male sterility located on chromosome 1A and a functional restorer gene allele for wheat G-type cytoplasmic male sterility located on chromosome 1B, comprising the steps of a. crossing a first cereal plant homozygous for a functional restorer gene for wheat G-type cytoplasmic male sterility located on chromosome 1A and homozygous for a functional restorer gene for wheat G-type cytoplasmic male sterility located on chromosome 1B, with a second cereal plant (wherein said first cereal plant comprises at least one marker allele linked to a functional restorer gene allele for wheat G-type cytoplasmic male sterility located on chromosome 1A and at least one marker allele linked to a functional restorer gene allele for wheat G-type cytoplasmic male sterility located on chromosome 1B as described herein, preferably wherein said plant is homozygous for said at least one 1A marker allele and for said at least one 1B marker allele)

b. obtaining a progeny plant, wherein said progeny plant comprises a functional restorer gene allele for wheat G-type cytoplasmic male sterility located on chromosome 1A and functional restorer gene allele for wheat G-type cytoplasmic male sterility located on chromosome 1B (wherein said progeny plant comprises at least one marker allele linked to a functional restorer gene allele for wheat G-type cytoplasmic male sterility located on chromosome 1A and at least one marker allele linked to a functional restorer gene allele for wheat G-type cytoplasmic male sterility located on chromosome 1B as described herein, and hence is identifiable using the methods described herein)

Said second plant can be a plant not comprising a functional restorer gene for wheat G-type cytoplasmic male sterility located on chromosome 1A and/or not comprising a functional restorer gene for wheat G-type cytoplasmic male sterility located on chromosome 1B.

In an even further embodiment, the invention provides a method for producing F1 hybrid seeds or F1 hybrid plants, comprising the steps of:

a. Providing a male cereal (e.g. wheat) parent plant comprising a functional restorer gene allele for wheat G-type cytoplasmic male sterility located on chromosome 1A and a functional restorer gene allele for wheat G-type cytoplasmic male sterility located on chromosome 1B;

b. Crossing said male parent plant with a female cereal (e.g. wheat) parent plant, wherein the female parent plant is a G-type cytoplasmic male sterile cereal plant;

c. Optionally collecting hybrid seeds from said cross.

The F1 hybrid seeds and plants preferably comprise at least one marker allele linked to a functional restorer gene allele for wheat G-type cytoplasmic male sterility located on chromosome 1A (1A restorer marker allele) and at least one marker allele linked to a functional restorer gene allele for wheat G-type cytoplasmic male sterility located on chromosome 1B as described herein, and the F1 plants grown from the seeds are therefore fertile (increased fertility compared to plants having only one of the two Rf loci). Preferably, the male parent plant is thus homozygous for said a functional restorer gene allele for wheat G-type cytoplasmic male sterility located on chromosome 1A and hence is also homozygous for said at least one 1A restorer marker allele, and/or is preferably homozygous for said a functional restorer gene allele for wheat G-type cytoplasmic male sterility located on chromosome 1B and hence is also homozygous for said at least one 1B restorer marker allele, even more preferably homozygous for both loci.

In the above method, the male parent plant used for crossing can be selected using any of the herein described methods for selecting a cereal plant comprising a functional restorer gene for wheat G-type cytoplasmic male sterility. Accordingly, the male parent plant comprises at least one marker allele linked to a functional restorer gene allele for wheat G-type cytoplasmic male sterility located on chromosome 1A, preferably in homozygous form, and at least one marker allele linked to a functional restorer gene allele for wheat G-type cytoplasmic male sterility located on chromosome 1B, preferably in homozygous form, even more preferable both in homozygous form.

The invention also provides cereal plants, such as wheat plants, obtained by any of the above methods, said cereal plant comprising at least one marker allele linked to the functional restorer gene allele for wheat G-type cytoplasmic male sterility located on chromosome 1A and at least one marker allele linked to the functional restorer gene allele for wheat G-type cytoplasmic male sterility located on chromosome 1B, as described herein.

Said at least one marker allele linked to the functional restorer gene allele for wheat G-type cytoplasmic male sterility located on chromosome 1A and said at least one marker allele linked to the functional restorer gene allele for wheat G-type cytoplasmic male sterility located on chromosome 1B may localize to the same chromosomal intervals or contigs and can be selected from the same groups as described above for the other embodiments and aspect.

Also described is a cereal plant, plant part, plant cell or seed comprising at least one functional restorer gene allele for wheat G-type cytoplasmic male sterility located on chromosome 1A and at least one functional restorer gene allele for wheat G-type cytoplasmic male sterility located on chromosome 1B, said plant comprising at least one marker allele linked to a functional restorer gene allele for wheat G-type cytoplasmic male sterility located on chromosome 1A (1A restorer marker allele), wherein said at least one marker allele localises within an interval on chromosome 1A comprising and flanked by the markers of SEQ ID NO. 2 and 4, preferably wherein said plant comprises one or more of, such as one, two, three, four, five, six, or all of:

a. an A at SEQ ID NO: 2;
b. a C at SEQ ID NO: 3;
c. a C at SEQ ID NO: 4;
d. a C at SEQ ID NO: 16;
e. a G at SEQ ID NO: 17;
f. a C at SEQ ID NO: 18;
g. a G at SEQ ID NO: 19;
said plant not comprising any one or all of
h. a G at SEQ ID NO: 1;
l. an A at SEQ ID NO: 5;
said plant further comprising at least one marker allele linked to a functional restorer gene allele for wheat G-type cytoplasmic male sterility located on chromosome 1B (1B restorer marker allele), wherein said at least one marker allele localises within an interval on chromosome 1B comprising and flanked by the markers of SEQ ID NO. 7 and 13, such as one, two, three, four, five, six, seven, eight, nine, ten or all of:

j. a T at SEQ ID NO: 7;
k. a C at SEQ ID NO: 8;
l. a T at SEQ ID NO: 9;
m. a T at SEQ ID NO: 10;
n. an A at SEQ ID NO: 11;
o. an A at SEQ ID NO: 12;
p. a G at SEQ ID NO: 13;
q. a C at SEQ ID NO: 22;
r. an A at SEQ ID NO: 23,
s. a T at SEQ ID NO: 24;
t. a T at SEQ ID NO: 25,
said plant not comprising any one or all of
u. an A at SEQ ID NO: 6;
v. a T at SEQ ID NO: 14.

Also described is a cereal plant, plant part, plant cell or seed comprising at least one functional restorer gene allele for wheat G-type cytoplasmic male sterility located on chromosome 1A at least one functional restorer gene allele for wheat G-type cytoplasmic male sterility located on chromosome 1B, said plant comprising at least one marker allele linked to a functional restorer gene allele for wheat G-type cytoplasmic male sterility located on chromosome 1A (1A restorer marker allele), wherein said at least one marker allele localises within an interval on chromosome 1A comprising and flanked by the markers of SEQ ID NO. 2 and 4, preferably wherein said plant comprises at least one of, such as one, two, three, four, five, six, or all of:
 a. an A at SEQ ID NO: 2;
 b. a C at SEQ ID NO: 3;
 c. a C at SEQ ID NO: 4;
 d. a C at SEQ ID NO: 16;
 e. a G at SEQ ID NO: 17;
 f. a C at SEQ ID NO: 18;
 g. a G at SEQ ID NO: 19;
 said plant not comprising any one or all of
 h. a G at SEQ ID NO. 1;
 l. an A at SEQ ID NO: 5;
said plant further comprising at least one marker allele linked to a functional restorer gene allele for wheat G-type cytoplasmic male sterility located on chromosome 1B (1B restorer marker allele), wherein said at least one marker allele localises within an interval on chromosome 1B comprising and flanked by the markers of SEQ ID NO. 22 and 25, preferably wherein said plant comprises at least one of, such as one, two, three or all of:
 j. a C at SEQ ID NO: 22;
 k. an A at SEQ ID NO: 23,
 l. a T at SEQ ID NO: 24;
 m. a T at SEQ ID NO: 25,
 said plant not comprising any one or all of
 n. a T at SEQ ID NO: 7;
 o. an G at SEQ ID NO: 13.

Also described is a cereal plant, plant part, plant cell or seed comprising at least one functional restorer gene allele for wheat G-type cytoplasmic male sterility located on chromosome 1A at least one functional restorer gene allele for wheat G-type cytoplasmic male sterility located on chromosome 1B, said plant comprising at least one marker allele linked to a functional restorer gene allele for wheat G-type cytoplasmic male sterility located on chromosome 1A (1A restorer marker allele), wherein said at least one marker allele localises within an interval on chromosome 1A comprising and flanked by the markers of SEQ ID NO. 2 and 4, preferably wherein said plant comprises at least one of, such as one, two, three, four, five, six, or all of:
 a. an A at SEQ ID NO: 2;
 b. a C at SEQ ID NO: 3;
 c. a C at SEQ ID NO: 4;
 d. a C at SEQ ID NO: 16;
 e. a G at SEQ ID NO: 17;
 f. a C at SEQ ID NO: 18;
 g. a G at SEQ ID NO: 19;
 said plant not comprising any one or all of
 h. a G at SEQ ID NO. 1;
 l. an A at SEQ ID NO: 5;
 said plant further comprising at least one marker allele linked to a functional restorer gene allele for wheat G-type cytoplasmic male sterility located on chromosome 1B (1B restorer marker allele), wherein said at least one marker allele localises within an interval on chromosome 1B comprising and flanked by the markers of SEQ ID NO. 22 and 25, preferably wherein said plant comprises at least one of, such as one, two, three or all of:
 j. a C at SEQ ID NO: 22;
 k. an A at SEQ ID NO: 23,
 i. a T at SEQ ID NO: 24;
 m. a T at SEQ ID NO: 25,
 said plant not comprising any one or all of
 n. a T at SEQ ID NO: 21;
 o. an T at SEQ ID NO: 10.

Also described is a cereal plant, plant part, plant cell or seed comprising at least one functional restorer gene allele for wheat G-type cytoplasmic male sterility located on chromosome 1A and at least one functional restorer gene allele for wheat G-type cytoplasmic male sterility located on chromosome 1B, said plant comprising at least one marker allele linked to a functional restorer gene allele for wheat G-type cytoplasmic male sterility located on chromosome 1A (1A restorer marker allele), wherein said at least one marker allele localises within an interval on chromosome 1A comprising and flanked by the markers of SEQ ID NO. 16 and 19, preferably wherein said plant comprises at least one of, such as one, two, three or all of:
 a. a C at SEQ ID NO: 16;
 b. a G at SEQ ID NO: 17;
 c. a C at SEQ ID NO: 18;
 d. a G at SEQ ID NO: 19;
 said plant not comprising any one or all of
 e. an A at SEQ ID NO. 2;
 f. a C at SEQ ID NO: 4;
said plant further comprising at least one marker allele linked to a functional restorer gene allele for wheat G-type cytoplasmic male sterility located on chromosome 1B (1B restorer marker allele), wherein said at least one marker allele localises within an interval on chromosome 1B comprising and flanked by the markers of SEQ ID NO. 7 and 13, preferably wherein said plant comprises at least one of, such as one, two, three, four, five, six, seven, eight, nine, ten or all of:
 g. a T at SEQ ID NO: 7;
 h. a C at SEQ ID NO: 8;
 i. a T at SEQ ID NO: 9;
 j. a T at SEQ ID NO: 10;
 k. an A at SEQ ID NO: 11;
 l. an A at SEQ ID NO: 12;
 m. a G at SEQ ID NO: 13;
 n. a C at SEQ ID NO: 22;
 o. an A at SEQ ID NO: 23,
 p. a T at SEQ ID NO: 24;
 q. a T at SEQ ID NO: 25,
 said plant not comprising any one or all of
 r. an A at SEQ ID NO: 6;
 s. a T at SEQ ID NO: 14.

Also described is cereal plant, plant part, plant cell or seed comprising at least one functional restorer gene allele for wheat G-type cytoplasmic male sterility located on chromosome 1A and at least one functional restorer gene allele for wheat G-type cytoplasmic male sterility located on chromosome 1B, said plant comprising at least one marker allele linked to a functional restorer gene allele for wheat G-type cytoplasmic male sterility located on chromosome 1A (1A restorer marker allele)), wherein said at least one marker allele localises within an interval on chromosome 1A comprising and flanked by the markers of SEQ ID NO. 16 and 19, preferably wherein said plant comprises at least one of such as one, two, three or all of:
 a. a C at SEQ ID NO: 16;
 b. a G at SEQ ID NO: 17;

c. a C at SEQ ID NO: 18;
d. a G at SEQ ID NO: 19;
said plant not comprising any one or all of
e. an A at SEQ ID NO. 2;
f. a C at SEQ ID NO: 4;
said plant further comprising at least one marker allele linked to a functional restorer gene allele for wheat G-type cytoplasmic male sterility located on chromosome 1B (1B restorer marker allele), wherein said at least one marker allele localises within an interval on chromosome 1B comprising and flanked by the markers of SEQ ID NO. 22 and 25, preferably wherein said plant comprises at least one of, such as one, two, three or all of:
g. a C at SEQ ID NO: 22;
h. an A at SEQ ID NO: 23,
i. a T at SEQ ID NO: 24;
j. a T at SEQ ID NO: 25,
said plant not comprising any one or all of
k. a T at SEQ ID NO: 7;
l. an G at SEQ ID NO: 13.

Also described is a cereal plant, plant part, plant cell or seed comprising at least one functional restorer gene allele for wheat G-type cytoplasmic male sterility located on chromosome 1A and at least one functional restorer gene allele for wheat G-type cytoplasmic male sterility located on chromosome 1B, said plant comprising at least one marker allele linked to a functional restorer gene allele for wheat G-type cytoplasmic male sterility located on chromosome 1A (1A restorer marker allele), wherein said at least one marker allele localises within an interval on chromosome 1A comprising and flanked by the markers of SEQ ID NO. 16 and 19, preferably wherein said plant comprises at least one of, such as one, two, three or all of:
a. a C at SEQ ID NO: 16;
b. a G at SEQ ID NO: 17;
c. a C at SEQ ID NO: 18;
d. a G at SEQ ID NO: 19;
said plant not comprising any one or all of
e. an A at SEQ ID NO. 2;
f. a C at SEQ ID NO: 4;
said plant further comprising at least one marker allele linked to a functional restorer gene allele for wheat G-type cytoplasmic male sterility located on chromosome 1B (1B restorer marker allele), wherein said at least one marker allele localises within an interval on chromosome 1B comprising and flanked by the markers of SEQ ID NO. 22 and 25, preferably wherein said plant comprises at least one of, such as one, two, three or all of:
g. a C at SEQ ID NO: 22;
h. an A at SEQ ID NO: 23,
i. a T at SEQ ID NO: 24;
j. a T at SEQ ID NO: 25,
said plant not comprising any one or all of
k. a T at SEQ ID NO: 21;
l. an T at SEQ ID NO: 10.

Also described are a cereal plant, plant part, plant cell or seed comprising at least one functional restorer gene allele for wheat G-type cytoplasmic male sterility located on chromosome 1A and at least one functional restorer gene allele for wheat G-type cytoplasmic male sterility located on chromosome 1B, said plant comprising at least one marker allele linked to a functional restorer gene allele for wheat G-type cytoplasmic male sterility located on chromosome 1A (1A restorer marker allele)), wherein said at least one marker allele localises within an interval on chromosome 1A comprising and flanked by the markers of SEQ ID NO. 16 and 19, preferably wherein said plant comprises at least one of, such as one, two, three or all of:
a. a C at SEQ ID NO: 16;
b. a G at SEQ ID NO: 17;
c. a C at SEQ ID NO: 18;
d. a G at SEQ ID NO: 19;
said plant not comprising any one or all of
e. a T at SEQ ID NO: 15;
f. a C at SEQ ID NO: 20;
said plant further comprising at least one marker allele linked to a functional restorer gene allele for wheat G-type cytoplasmic male sterility located on chromosome 1B (1B restorer marker allele), wherein said at least one marker allele localises within an interval on chromosome 1B comprising and flanked by the markers of SEQ ID NO. 7 and 13, preferably wherein said plant comprises at least one of, such as one, two, three, four, five, six, seven, eight, nine, ten or all of:
g. a T at SEQ ID NO: 7;
h. a C at SEQ ID NO: 8;
i. a T at SEQ ID NO: 9;
j. a T at SEQ ID NO: 10;
k. an A at SEQ ID NO: 11;
l. an A at SEQ ID NO: 12;
m. a G at SEQ ID NO: 13;
n. a C at SEQ ID NO: 22;
o. an A at SEQ ID NO: 23,
p. a T at SEQ ID NO: 24;
q. a T at SEQ ID NO: 25,
said plant not comprising any one or all of
r. an A at SEQ ID NO: 6;
s. a T at SEQ ID NO: 14.

Also described are a cereal plant, plant part, plant cell or seed comprising at least one functional restorer gene allele for wheat G-type cytoplasmic male sterility located on chromosome 1A and at least one functional restorer gene allele for wheat G-type cytoplasmic male sterility located on chromosome 1B, said plant comprising at least one marker allele linked to a functional restorer gene allele for wheat G-type cytoplasmic male sterility located on chromosome 1A (1A restorer marker allele), wherein said at least one marker allele localises within an interval on chromosome 1A comprising and flanked by the markers of SEQ ID NO. 16 and 19, preferably wherein said plant comprises at least one of, such as one, two, three or all of:
a. a C at SEQ ID NO: 16;
b. a G at SEQ ID NO: 17;
c. a C at SEQ ID NO: 18;
d. a G at SEQ ID NO: 19;
said plant not comprising any one or all of
e. a T at SEQ ID NO: 15;
f. a C at SEQ ID NO: 20;
said plant further comprising at least one marker allele linked to a functional restorer gene allele for wheat G-type cytoplasmic male sterility located on chromosome 1B (1B restorer marker allele), wherein said at least one marker allele localises within an interval on chromosome 1B comprising and flanked by the markers of SEQ ID NO. 22 and 25, preferably wherein said plant comprises at least one of, such as one, two, three or all of:
g. a C at SEQ ID NO: 22;
h. an A at SEQ ID NO: 23,
i. a T at SEQ ID NO: 24;
j. a T at SEQ ID NO: 25,
said plant not comprising any one or all of
k. a T at SEQ ID NO: 7;
l. an G at SEQ ID NO: 13.

Also described are a cereal plant, plant part, plant cell or seed comprising at least one functional restorer gene allele for wheat G-type cytoplasmic male sterility located on chromosome 1A and at least one functional restorer gene allele for wheat G-type cytoplasmic male sterility located on chromosome 1B, said plant comprising at least one marker allele linked to a functional restorer gene allele for wheat G-type cytoplasmic male sterility located on chromosome 1A (1A restorer marker allele)), wherein said at least one marker allele localises within an interval on chromosome 1A comprising and flanked by the markers of SEQ ID NO. 16 and 19, preferably wherein said plant comprises at least one of, such as one, two, three or all of:
  a. a C at SEQ ID NO: 16;
  b. a G at SEQ ID NO: 17;
  c. a C at SEQ ID NO: 18;
  d. a G at SEQ ID NO: 19;
  said plant not comprising any one or all of
  e. a T at SEQ ID NO: 15;
  f. a C at SEQ ID NO: 20;
  said plant further comprising at least one marker allele linked to a functional restorer gene allele for wheat G-type cytoplasmic male sterility located on chromosome 1B (1B restorer marker allele), wherein said at least one marker allele localises within an interval on chromosome 1B comprising and flanked by the markers of SEQ ID NO. 22 and 25, preferably wherein said plant comprises at least one of, such as one, two, three or all of:
  g. a C at SEQ ID NO: 22;
  h. an A at SEQ ID NO: 23,
  i. a T at SEQ ID NO: 24;
  j. a T at SEQ ID NO: 25,
  said plant not comprising any one or all of
  k. a T at SEQ ID NO: 21;
  l. an T at SEQ ID NO: 10.

In a further embodiment, any of the above plants plant part, plant cell or seeds comprises a C at SEQ ID NO. 18 and/or a Tat SEQ ID NO. 24 (preferably both). In an even further embodiment, said plant, plant part, plant cell or seeds comprising a C at SEQ ID NO. 18 and/or a Tat SEQ ID NO. 24 does not comprise any one or all of
  a. a C at SEQ ID NO: 16;
  b. a G at SEQ ID NO: 17;
  c. a G at SEQ ID NO: 19; and/or
  d. a C at SEQ ID NO: 22;
  e. an A at SEQ ID NO: 23
  f. a T at SEQ ID NO: 25, Also provided are plant parts, plant cells and seed from the cereal plants according to the invention comprising said at least one 1A restorer marker allele and said 1A functional restorer gene allele, as well as said at least one 1B restorer marker allele and said 1B functional restorer gene allele, as described herein. The plants, plant parts, plant cells and seeds of the invention may also be hybrid plants, plant parts, plant cells or seeds.

Also provided is a method to determine the presence or absence or zygosity status of a functional restorer gene allele for wheat G-type cytoplasmic male sterility located on chromosome 1A and presence or absence or zygosity status of a functional restorer gene allele for wheat G-type cytoplasmic male sterility located on chromosome 1B in a biological sample of a cereal plant, comprising providing genomic DNA from said biological sample, and analysing said DNA for the presence or absence or zygosity status of at least one marker allele linked to a functional restorer gene for wheat G-type cytoplasmic male sterility located on chromosome 1A for the presence or absence or zygosity status of at least one marker allele linked to a functional restorer gene for wheat G-type cytoplasmic male sterility located on chromosome 1B as described herein. It will be clear that the presence can be determined using a marker allele linked to the functional restorer gene allele as described herein, whereas the absence can (additionally) be determined by detecting the presence of the other, non-restoring allele of said marker. The zygosity status, i.e. whether the plant is homozygous for one or both of the restorer allele, homozygous for one or both the non-restorer allele or for one or both heterozygous (i.e. the Rf genotype), can be determined by detecting the presence or absence of a marker allele linked to the functional restorer gene and by detecting the presence of the other, non-restoring allele, but depending on the parental origin it can also be sufficient to determine the presence or absence of only one of the alleles to be able to deduce the complete genotype (zygosity status) of the plant.

The invention also provides the use of at least one marker comprising an allele linked to the functional restorer gene for wheat G-type cytoplasmic male sterility located on chromosome 1A and at least one marker allele linked to a functional restorer gene for wheat G-type cytoplasmic male sterility located on chromosome 1B for the identification of at least one further marker comprising an allele linked to said functional restorer gene for wheat G-type cytoplasmic male sterility located on chromosome 1A and at least one further marker allele linked to a functional restorer gene for wheat G-type cytoplasmic male sterility located on chromosome 1B, respectively. Such markers are also genetically linked or tightly linked to the restorer gene, and are also within the scope of the invention. Markers can be identified by any of a variety of genetic or physical mapping techniques. Methods of determining whether markers are genetically linked to a restore gene are known to those of skill in the art and include, for example, interval mapping (Lander and Botstein, (1989) Genetics 121:185), regression mapping (Haley and Knott, (1992) Heredity 69:315) or MQM mapping (Jansen, (1994) Genetics 138:871), rMQM mapping. In addition, such physical mapping techniques as chromosome walking, contig mapping and assembly, amplicon resequencing, transcriptome sequencing, targeted capture and sequencing, next generation sequencing and the like, can be employed to identify and isolate additional sequences useful as markers in the context of the present invention.

The invention further provides the use of at least one marker allele linked to a functional restorer gene for wheat G-type cytoplasmic male sterility located on chromosome 1A and at least one marker allele linked to a functional restorer gene for wheat G-type cytoplasmic male sterility located on chromosome 1B as described herein for the identification of a plant a comprising said functional restorer gene alleles for wheat G-type cytoplasmic male sterility located on chromosome 1A and 1B.

Also provided is the use of a plant obtained by any of the methods as described herein and comprising at least one marker allele linked to a functional restorer gene for wheat G-type cytoplasmic male sterility located on chromosome 1A and at least one marker allele linked to a functional restorer gene for wheat G-type cytoplasmic male sterility located on chromosome 1B as described herein, for (increased) restoration of fertility in a progeny of a G-type cytoplasmic male sterile cereal plant, such as a wheat plant, or for producing a population of hybrid cereal plants, such as a wheat plants.

Further provided is a method for identifying a functional restorer gene allele for wheat G-type cytoplasmic male sterility located on chromosome 1A, comprising the steps of
a. Providing a population of F2 plants resulting from selfing of a population of F1 plants obtained by crossing a female cereal parent plant with a male cereal parent plant, wherein the female parent plant is a G-type cytoplasmic male sterile cereal plant, and wherein the male parent plant comprises a functional restorer gene allele for wheat G-type cytoplasmic male sterility located on chromosome 1A
b. Classifying the fertility of a plurality of said F2 plants
c. Determining the nucleotide sequence of at least part of the region of chromosome 1A comprising and flanked by the markers of SEQ ID NO 2 and SEQ ID NO 4 of genomic DNA isolated from each of said plurality of F2 plants
d. Identifying the coding sequence within said region having the highest association to the phenotype of restored fertility, wherein the identified coding sequence is the functional restorer gene allele for wheat G-type cytoplasmic male sterility located on chromosome 1A Further provided is a method for identifying a functional restorer gene allele for wheat G-type cytoplasmic male sterility located on chromosome 1B, comprising the steps of
a. Providing a population of F2 plants resulting from selfing of a population of F1 plants obtained by crossing a female cereal parent plant with a male cereal parent plant, wherein the female parent plant is a G-type cytoplasmic male sterile cereal plant, and wherein the male parent plant comprises a functional restorer gene allele for wheat G-type cytoplasmic male sterility located on chromosome 1B
b. Classifying the fertility of a plurality of said F2 plants
c. Determining the nucleotide sequence of at least part of the region of chromosome 1B comprising and flanked by the markers of SEQ ID NO 7 and SEQ ID NO 13 of genomic DNA isolated from each of said plurality of F2 plants
d. Identifying the coding sequence within said region having the highest association the phenotype of restored fertility, wherein the identified coding sequence is the functional restorer gene allele for wheat G-type cytoplasmic male sterility located on chromosome 1B In any of the above described methods or uses, the markers and marker alleles can localize to the same chromosomal intervals and can be selected from the same groups as described above for the other embodiments and aspect.

Also provided are any of the markers comprising an allele linked to the functional restorer gene for wheat G-type cytoplasmic male sterility located on chromosome 1A and any of the markers comprising an allele linked to the functional restorer gene for wheat G-type cytoplasmic male sterility located on chromosome 1B, as described herein.

Also provided herein is a chromosome fragment which comprises a functional restorer gene for wheat G-type cytoplasmic male sterility located on chromosome 1A and a chromosome fragment which comprises a functional restorer gene for wheat G-type cytoplasmic male sterility located on chromosome 1B, as described throughout the specification (A combination of chromosome fragments). In one aspect the chromosome fragments are isolated from its natural environment. In another aspect they are in a plant cell, especially in a cereal cell, especially in a wheat cell. Also an isolated part of the chromosome fragments comprising the functional restorer gene alleles for wheat G-type cytoplasmic male sterility is provided herein. Such chromosome fragments can for example be a contig or a scaffold.

Further provided is a recombinant nucleic acid molecule, especially a recombinant DNA molecule, which comprises a functional 1A restorer gene allele according to the invention and a recombinant nucleic acid molecule, especially a recombinant DNA molecule, which comprises a functional 1B restorer gene allele according to the invention. In one aspect the functional restorer gene alleles are detectable by one or more of the molecular marker assays described herein. Also DNA vectors are provided comprising the recombinant DNAs. The recombinant DNA molecules or DNA vectors may be isolated nucleic acid molecules. The recombinant or isolated DNA molecules may also be present on one vector, i.e. one vector comprising both an isolated DNA molecule functional 1A restorer gene allele and an isolated DNA molecule functional 1B restorer gene allele. The DNA comprising the functional restorer gene alleles may be in a microorgansims, such as a bacterium (e.g. *Agrobacterium*).

Thus, in one embodiment, the invention provides an isolated nucleic acid molecule encoding a functional restorer gene allele for wheat G-type cytoplasmic male sterility, wherein said functional restorer gene allele localises within an interval on chromosome 1A comprising and flanked by the markers of SEQ ID NO 2 and SEQ ID NO 4 and an isolated nucleic acid molecule encoding a functional restorer gene allele for wheat G-type cytoplasmic male sterility, wherein said functional restorer gene allele localises within an interval on chromosome 1B comprising and flanked by the markers of SEQ ID NO 7 and SEQ ID NO 13. Thus, the isolated nucleic acid molecule encodes or comprises a functional restorer gene allele for wheat G-type cytoplasmic male sterility that is derivable or derived from an interval on chromosome 1A comprising and flanked by the markers of SEQ ID NO 2 and SEQ ID NO 4 or from an interval on chromosome 1B comprising and flanked by the markers of SEQ ID NO 7 and SEQ ID NO 13 respectively. Said functional restorer gene alleles can be identified using any of the marker alleles linked to said functional restorer gene allele as described herein.

In a further embodiment, said functional restorer gene allele encoded by said isolated nucleic acid molecule localizes within an interval on chromosome 1A comprising and flanked by the markers of SEQ ID NO. 16 and SEQ ID NO. 19.

In a further embodiment, said functional restorer gene allele encoded by said isolated nucleic acid molecule localizes within an interval on chromosome 1B comprising and flanked by the markers of SEQ ID NO 22 and SEQ ID NO 25.

In a further embodiment, said functional restorer gene alleles encoded by said isolated nucleic acid molecules are obtainable from USDA accession number PI 583676.

Also provided are isolated polypeptides encoding functional 1A and 1B restorer alleles encoded by the nucleic acid molecule as described above.

The functional restorer gene alleles may also be cloned and a chimeric gene may be made, e.g. by operably linking a plant expressible promoter to the functional restorer gene allele and optionally a 3' end region involved in transcription termination and polyadenylation functional in plants. Such chimeric genes may be introduced into a plant cell, and the plant cell may be regenerated into a whole plant to produce a transgenic plant. In one aspect the transgenic plant is a cereal plant, such as a wheat plant, according to any method well known in the art.

Thus, in a particular embodiment a chimeric gene is provided comprising an isolated nucleic acid molecule encoding the functional 1A restorer gene allele and a chimeric gene comprising an isolated nucleic acid molecule encoding the functional 1B restorer gene allele as described above, operably linked to a heterologous plant-expressible promoter and optionally a 3' termination and polyadenylation region. Such chimeric genes may be present on one vector, i.e. a vector comprising a chimeric gene encoding the 1A restorer gene allele and a chimeric gene encoding the 1B restorer gene allele, but also on separate vectors.

The use of such a (isolated or extracted) nucleic acid molecule and/or of such a chimeric gene and/or of such a chromosome fragment for generating plant cells and plants comprising functional 1A and 1B restorer gene alleles is encompassed herein. In one aspect they may be used to generate transgenic cereal (e.g. wheat) cells, plants and plant parts or seeds comprising the functional restorer gene alleles and the plant having the (increased) capacity to restore fertility against wheat G-type cytoplasmic male sterility as described above.

Thus, also provided is a method for producing a cereal plant cell or plant or seed thereof, such as a wheat plant cell or plant or seed thereof, comprising a functional 1A restorer gene allele and a functional 1B restorer gene allele, comprising the steps of providing said plant cell or plant with the recombinant chromosome fragments or the isolated nucleic acid molecules or the chimeric genes or the vectors as described herein, wherein said providing comprises transformation, crossing, backcrossing, genome editing or mutagenesis.

Thus, transgenic cereal cells, e.g. transgenic wheat cells, comprising in their genome the recombinant chromosome fragments as described or the isolated nucleic acid molecules as described or the chimeric genes or vectors as described comprising the functional 1A restorer gene allele and the functional 1B restore allele as described are also an embodiment of the invention. In one aspect the DNA molecules comprising the functional 1A and 1B Rf alleles are stably integrated into the cereal (e.g. wheat) genome, preferably close together on one chromosome (linked or tightly linked) so that they inherit as a single genetic unit.

Thus, cereal plants, plant parts, plant cells, or seeds thereof, especially wheat, comprising chromosome fragments or nucleic acid molecules according to the invention or polypeptides according to the invention or chimeric genes or vectors according to the invention encoding a functional 1A and 1B restorer gene alleles according to the invention, are provided, said plant having the (increased) capacity to restore fertility against wheat G-type cytoplasmic male sterility are provided herein. In one embodiment, the chromosome fragments, nucleic acid molecules, polypeptides or chimeric genes or vectors are heterologous to the plant, such as transgenic cereal plants or transgenic wheat plants. This also includes plant cells or cell cultures comprising such chromosome fragments or nucleic acid molecules, polypeptides or chimeric genes or vectors, independent whether introduced by transgenic methods or by breeding methods. The cells are e.g. in vitro and are regenerable into plants comprising the chromosome fragment or chimeric gene of the invention. Said plants, plant parts, plant cells and seeds may also be hybrid plants, plant parts, plant cells or seeds.

Such plants may also be used as male parent plant in a method for producing F1 hybrid seeds or F1 hybrid plants, as described above.

A plant-expressible promoter as used herein can be any promoter that drives sufficient expression at least in pollen tissue. This can for example be a constitutive promoter, an inducible promoter, but also a pollen- or microspore-specific/preferential promoter.

A constitutive promoter is a promoter capable of directing high levels of expression in most cell types (in a spatiotemporal independent manner). Examples of plant expressible constitutive promoters include promoters of bacterial origin, such as the octopine synthase (OCS) and nopaline synthase (NOS) promoters from *Agrobacterium*, but also promoters of viral origin, such as that of the cauliflower mosaic virus (CaMV) 35S transcript (Hapster et al., 1988, Mol. Gen. Genet. 212: 182-190) or 19S RNAs genes (Odell et al., 1985, Nature. 6; 313(6005):810-2; U.S. Pat. No. 5,352,605; WO 84/02913; Benfey et al., 1989, EMBO J. 8:2195-2202), the enhanced 2×35S promoter (Kay at al., 1987, Science 236:1299-1302; Datla et al. (1993), Plant Sci 94:139-149) promoters of the cassava vein mosaic virus (CsVMV; WO 97/48819, U.S. Pat. No. 7,053,205), 2×CsVMV (WO2004/053135) the circovirus (AU 689 311) promoter, the sugarcane bacilliform badnavirus (ScBV) promoter (Samac et al., 2004, Transgenic Res. 13(4):349-61), the figwort mosaic virus (FMV) promoter (Sanger et al., 1990, Plant Mol Biol. 14(3):433-43), the subterranean clover virus promoter No 4 or No 7 (WO 96/06932) and the enhanced 35S promoter as described in U.S. Pat. Nos. 5,164,316, 5,196,525, 5,322,938, 5,359,142 and 5,424,200. Among the promoters of plant origin, mention will be made of the promoters of the plant ribulose-biscarboxylase/oxygenase (Rubisco) small subunit promoter (U.S. Pat. No. 4,962,028; WO99/25842) from *Zea mays* and sunflower, the promoter of the *Arabidopsis thaliana* histone H4 gene (Chabouté et al., 1987), the ubiquitin promoters (Holtorf et al., 1995, Plant Mol. Biol. 29:637-649, U.S. Pat. No. 5,510, 474) of Maize, Rice and sugarcane, the Rice actin 1 promoter (Act-1, U.S. Pat. No. 5,641,876), the histone promoters as described in EP 0 507 698 A1, the Maize alcohol dehydrogenase 1 promoter (Adh-1) (from world wide web at patentlens.net/daisy/promoters/242.html)). Also the small subunit promoter from *Chrysanthemum* may be used if that use is combined with the use of the respective terminator (Outchkourov et al., Planta, 216: 1003-1012, 2003).

Pollen/microspore-active promoters include e.g. a maize pollen specific promoter (see, e.g., Guerrero (1990) Mol. Gen. Genet. 224:161 168), PTA29, PTA26 and PTAI 3 (e.g., see U.S. Pat. No. 5,792,929) and as described in e.g. Baerson et al. (1994 Plant Mol. Biol. 26: 1947-1959), the NMT19 microspore-specific promoter as e.g. described in WO97/30166. Further pollen-specific or pollen-active promoters are described in e.g. Khurana et al., 2012 (Critical Reviews in Plant Sciences, 31: 359-390), WO2005100575, WO 2008037436.

It will be clear that the herein identified nucleic acids and polypeptides encoding functional restorer genes can be used to identify further functional restorer genes for wheat G-type cytoplasmic male sterility. Thus, the invention also provides the use of the isolated nucleic acids or polypeptides as disclosed herein to identify one or more further functional restorer genes for wheat G-type cytoplasmic male sterility.

Further, homologous or substantially identical functional restorer genes can be identified using methods known in the art. Homologous nucleotide sequence may be identified and isolated by hybridization under stringent or high stringent conditions using as probes a nucleic acid comprising e.g. the nucleotide sequences or part thereof, as described herein. Other sequences encoding functional restorer genes may also be obtained by DNA amplification using oligonucleotides specific for genes encoding functional restorer genes as primers, such as but not limited to oligonucleotides comprising or consisting of about 20 to about 50 consecutive nucleotides of the nucleotide sequences as described herein or its complement. Homologous or substantially identical functional restorer genes can be identified in silico using Basic Local Alignment Search Tool (BLAST) homology search with the nucleotide or amino acid sequences as provided herein.

Functionality of restorer genes or alleles thereof, such as identified as above, can be validated for example by providing, e.g. by transformation or crossing, such restorer genes under control of a plant-expressible promoter in a cereal (wheat) plant that does not have the capacity to restore fertility of offspring of a G-type cytoplasmic male sterile wheat plant, crossing the thus generated cereal plant with a G-type cytoplasmic male sterile wheat plant and evaluating seed set in the progeny. Alternatively, a restorer line can be transformed with an RNAi construct or gene-edited with e.g. CRISPR-Cas technology or any other sequence specific nuclease so to generate a loss of function that renders the plant non-restoring. Similarly, other means for mutating the restorer gene (e.g. EMS, g-radiation) can be used to evaluate the effect of a loss of function mutation on restoring ability.

In any of the herein described embodiments and aspects the plant may comprise or may be selected to comprise or may be provided with a further functional restorer gene for wheat G-type cytoplasmic male sterility (located on or obtainable from the same or another chromosome), such as Rf2 (7D), Rf4 (6B), Rf5 (6D), Rf6 (5D), Rf7 (7B), Rf8, 6AS or 6BS (Tahir & Tsunewaki, 1969; Yen et al., 1969; Bahl & Maan, 1973; Du et al., 1991; Sihna et al., 2013; Ma et al., 1991; Zhou et al., 2005).

As used herein a "chimeric gene" refers to a nucleic acid construct which is not normally found in a plant species. A chimeric nucleic acid construct can be DNA or RNA. "Chimeric DNA construct" and "chimeric gene" are used interchangeably to denote a gene in which the promoter or one or more other regulatory regions, such as the a transcription termination and polyadenylation region of the gene are not associated in nature with part or all of the transcribed DNA region, or a gene which is present in a locus in the plant genome in which it does not occur naturally or present in a plant in which it does not naturally occur. In other words, the gene and the operably-linked regulatory region or the gene and the genomic locus or the gene and the plant are heterologous with respect to each other, i.e. they do not naturally occur together.

A first nucleotide sequence is "operably linked" with a second nucleic acid sequence when the first nucleic acid sequence is in a functional relationship with the second nucleic acid sequence. For example, a promoter is operably linked to a coding sequence if the promoter affects the transcription or expression of the coding sequence. When recombinantly produced, operably linked nucleic acid sequences are generally contiguous, and, where necessary to join two protein-coding regions, in the same reading frame (e.g., in a polycistronic ORF). However, nucleic acids need not be contiguous to be operably linked.

"Backcrossing" refers to a breeding method by which a (single) trait, such as fertility restoration (Rf), can be transferred from one genetic background (a "donor") into another genetic background (also referred to as "recurrent parent"), e.g. a plant not comprising such an Rf gene or locus. An offspring of a cross (e.g. an F1 plant obtained by crossing an Rf containing with an Rf lacking plant; or an F2 plant or F3 plant, etc., obtained from selfing the F1) is "backcrossed" to the parent. After repeated backcrossing (BC1, BC2, etc.) and optionally selfings (BC1S1, BC2S1, etc.), the trait of the one genetic background is incorporated into the other genetic background.

"Marker assisted selection" or "MAS" is a process of using the presence of molecular markers, which are genetically linked to a particular locus or to a particular chromosome region (e.g. introgression fragment), to select plants for the presence of the specific locus or region (introgression fragment). For example, a molecular marker genetically and physically linked to an Rf locus, can be used to detect and/or select plants comprising the Rf locus. The closer the genetic linkage of the molecular marker to the locus, the less likely it is that the marker is dissociated from the locus through meiotic recombination.

"LOD-score" (logarithm (base 10) of odds) refers to a statistical test often used for linkage analysis in animal and plant populations. The LOD score compares the likelihood of obtaining the test data if the two loci (molecular markers loci and/or a phenotypic trait locus) are indeed linked, to the likelihood of observing the same data purely by chance. Positive LOD scores favor the presence of linkage and a LOD score greater than 3.0 is considered evidence for linkage. A LOD score of +3 indicates 1000 to 1 odds that the linkage being observed did not occur by chance.

A "biological sample" can be a plant or part of a plant such as a plant tissue or a plant cell.

"Providing genomic DNA" as used herein refers to providing a sample comprising genomic DNA from the plant. The sample can refer to a tissue sample which has been obtained from said plant, such as, for example, a leaf sample, comprising genomic DNA from said plant. The sample can further refer to genomic DNA which is obtained from a tissue sample, such as genomic DNA which has been obtained from a tissue, such as a leaf sample. Providing genomic DNA can include, but does not need to include, purification of genomic DNA from the tissue sample. Providing genomic DNA thus also includes obtaining tissue material from a plant or larger piece of tissue and preparing a crude extract or lysate therefrom.

"Isolated DNA" as used herein refers to DNA not occurring in its natural genomic context, irrespective of its length and sequence. Isolated DNA can, for example, refer to DNA which is physically separated from the genomic context, such as a fragment of genomic DNA. Isolated DNA can also be an artificially produced DNA, such as a chemically synthesized DNA, or such as DNA produced via amplification reactions, such as polymerase chain reaction (PCR) well-known in the art. Isolated DNA can further refer to DNA present in a context of DNA in which it does not occur naturally. For example, isolated DNA can refer to a piece of DNA present in a plasmid. Further, the isolated DNA can refer to a piece of DNA present in another chromosomal context than the context in which it occurs naturally, such as for example at another position in the genome than the natural position, in the genome of another species than the species in which it occurs naturally, or in an artificial chromosome.

Whenever reference to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents (especially the restoring capacity), such as seed obtained by selfing or crossing, e.g. hybrid seed (obtained by crossing two inbred parental lines), hybrid plants and plant parts derived there from are encompassed herein, unless otherwise indicated.

In some embodiments, the plant cells of the invention may be non-propagating cells.

The obtained plants according to the invention can be used in a conventional breeding scheme to produce more plants with the same characteristics or to introduce the characteristic of the presence of the restorer gene according to the invention in other varieties of the same or related plant species, or in hybrid plants. The obtained plants can further be used for creating propagating material. Plants according to the invention can further be used to produce gametes, seeds, flour, embryos, either zygotic or somatic, progeny or hybrids of plants obtained by methods of the invention. Seeds obtained from the plants according to the invention are also encompassed by the invention.

"Creating propagating material", as used herein, relates to any means know in the art to produce further plants, plant parts or seeds and includes inter alia vegetative reproduction methods (e.g. air or ground layering, division, (bud) grafting, micropropagation, stolons or runners, storage organs such as bulbs, corms, tubers and rhizomes, striking or cutting, twin-scaling), sexual reproduction (crossing with another plant) and asexual reproduction (e.g. apomixis, somatic hybridization).

Transformation, as used herein, means introducing a nucleotide sequence into a plant in a manner to cause stable or transient expression of the sequence. Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; microinjection of plant cells; micro-projectile bombardment of plant cells; vacuum infiltration; and *Agrobacterium*-mediated transformation.

As used herein, the term "homologous" or "substantially identical" may refer to nucleotide sequences that are more than 85% identical. For example, a substantially identical nucleotide sequence may be 85.5%; 86%; 87%; 88%; 89%; 90%; 91%; 92%; 93%; 94%; 95%; 96%; 97%; 98%; 99% or 99.5% identical to the reference sequence. A probe may also be a nucleic acid molecule that is "specifically hybridizable" or "specifically complementary" to an exact copy of the marker to be detected ("DNA target"). "Specifically hybridizable" or "specifically complementary" are terms that indicate a sufficient degree of complementarity such that stable and specific binding occurs between the nucleic acid molecule and the DNA target. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired, for example, under stringent hybridization conditions, preferably highly stringent conditions.

"Stringent hybridization conditions" can be used to identify nucleotide sequences, which are homologous or substantially identical to a given nucleotide sequence. Stringent conditions are sequence dependent and will be different in different circumstances. Generally, stringent conditions are selected to be about 5° C. lower than the thermal melting point ($T_m$) for the specific sequences at a defined ionic strength and pH. The $T_m$ is the temperature (under defined ionic strength and pH) at which 50% of the target sequence hybridizes to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g. 100 nt) are for example those which include at least one wash in 0.2×SSC at 63° C. for 20 min, or equivalent conditions.

"High stringency conditions" can be provided, for example, by hybridization at 65° C. in an aqueous solution containing 6×SSC (20×SSC contains 3.0 M NaCl, 0.3 M Na-citrate, pH 7.0), 5×Denhardt's (100×Denhardt's contains 2% Ficoll, 2% Polyvinyl pyrollidone, 2% Bovine Serum Albumin), 0.5% sodium dodecyl sulphate (SDS), and 20 µg/ml denaturated carrier DNA (single-stranded fish sperm DNA, with an average length of 120-3000 nucleotides) as non-specific competitor. Following hybridization, high stringency washing may be done in several steps, with a final wash (about 30 min) at the hybridization temperature in 0.2-0.1×SSC, 0.1% SDS.

"Moderate stringency conditions" refers to conditions equivalent to hybridization in the above described solution but at about 60-62° C. Moderate stringency washing may be done at the hybridization temperature in 1×SSC, 0.1% SDS.

"Low stringency" refers to conditions equivalent to hybridization in the above described solution at about 50-52° C. Low stringency washing may be done at the hybridization temperature in 2×SSC, 0.1% SDS. See also Sambrook et al. (1989) and Sambrook and Russell (2001).

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol Biol 48(3):443-53) in The European Molecular Biology Open Software Suite (EMBOSS, Rice et al., 2000, Trends in Genetics 16(6): 276-277; see e.g. world wide web at ebi.ac.uk/emboss/align/index.html) using default settings (gap opening penalty=10 (for nucleotides)/10 (for proteins) and gap extension penalty=0.5 (for nucleotides)/0.5 (for proteins)). For nucleotides the default scoring matrix used is EDNAFULL and for proteins the default scoring matrix is EBLOSUM62. It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a nucleic acid which is functionally or structurally defined, may comprise additional DNA regions etc.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

All patents, patent applications, and publications or public disclosures (including publications on internet) referred to or cited herein are incorporated by reference in their entirety.

The sequence listing contained in the file named "BCS16-2011_ST25.txt", which is 9 kilobytes (size as measured in Microsoft Windows®), contains 25 sequences SEQ ID NO: 1 through SEQ ID NO: 25, is filed herewith by electronic submission and is incorporated by reference herein.

The invention will be further described with reference to the examples described herein; however, it is to be understood that the invention is not limited to such examples.

EXAMPLES

Example 1: Plant Materials and Genetic Mapping

A male sterile line carrying *Triticum timopheevii* CMS, CMS005, and a male sterile restorer line responding to *Triticum timopheevii* CMS (*T. timopheevii*/2* Iovvin//2* Quivira, Accession number PI 583676, USDA National Small Grains Collection; world wide web at ars.usda.gov/Main/docs.htm?docid=21891, also known as Dekalb 582M and registered as US PVP 7400045, available via the National Plant Germplasm System world wide web at npgsweb.ars-grin.gov/gringlobal/accessiondetail.aspx?id=1478647), were used as parents to generate F1 progeny. The F1 progeny was selfed to generate an F2 population. The F2 population, consisting of 281 individuals, was used for identification of the markers linked to the restorer locus. A genetic map with total of 2080 SNP markers was established and covered all chromosomes of the wheat genome. The chromosome 1A/is described by 108 SNP markers.

Example 2: Fertility Classification and Coarse Mapping

The 276 plants in this F2 population were phenotypically classified according to seed set on the main, bagged head. Plants without seeds under the bag were classified as sterile. Plants with seed set were classified as fertile. FIG. 1 details the number of F2s per amount of seeds set on a single head for 2 different locations. 41 and 45 F2 plants in the 2 locations, were classified as sterile. Fully sterile F2 plants were noticed in the 2 locations.

Using a genetic map of 2080 SNP, QTL analysis was carried out using Haley-Knott regression to test the effect of variation in seed set across all markers. Significant marker-trait associations are distinguished by −log-transformed p-values higher than 3. Such, an interval of significantly associated markers was delineated, including left and right flanking markers (SEQ ID NO. 2 and SEQ ID NO. 4 for 1A, SEQ ID NO. 7 and 13. The marker with the highest significance and biggest effect on restoration is the peak marker of SEQ ID NO. 3 for 1A and the peak marker of SEQ ID NO. 11 for 1B (as indicated by X in Table 1 below). An interval of significantly associated markers was delineated using the following criteria: significance threshold at 2.5, significance drop at 1.5 and significance drop between peaks at 2. This delimited the interval to 15.6 cM for 1A and 15.8 cM for 1B by the left and right flanking markers (FIG. 2).

TABLE 1

A: Markers in the interval with significance of marker-trait association and effect size on restoration (in number of seeds above average seed set in the entire population) on 1A.

| SEQ ID NO | Rf donor allele | SNP position in SEQ ID NO | Chromosome position (cM) | Significance (−log10(p)) | Significance interval | mean seed set | additive effect on seed set | dominance effect on seed set | phenotypic variance explained |
|---|---|---|---|---|---|---|---|---|---|
| 1 | G | 101 | 31.545 | 21.4 |   | 29.28 | 14.48 | 7 | 0.31 |
| 2 | A | 51 | 31.726 | 21.42 | x | 29.28 | 14.49 | 7 | 0.31 |
| 3 | C | 51 | 34.154 | 24.46 | x | 28.98 | 15.47 | 7.3 | 0.35 |
| 4 | C | 51 | 47.307 | 11.9 | x | 31.08 | 12.39 | 2 | 0.2 |
| 5 | A | 51 | 48.614 | 11.04 |   | 31.09 | 11.99 | 2.04 | 0.18 |

B: Markers in the interval with significance of marker-trait association and effect size on restoration (in number of seeds above average seed set in the entire population) on 1B.

| SEQ ID NO | Rf donor allele | SNP position in SEQ ID NO | Chromosome position (cM) | Significance (−log10(p)) | Significance interval | mean seed set | additive effect on seed set | dominance effect on seed set | phenotypic variance explained |
|---|---|---|---|---|---|---|---|---|---|
| 6 | A | 51 | 35.206 | 7.51 |   | 31.68 | 10.05 | 1.02 | 0.13 |
| 7 | T | 51 | 35.753 | 8.2 | x | 31.4 | 10.51 | 1.32 | 0.14 |

TABLE 1-continued

| 8  | C | 51 | 38.165 | 10.49 | x | 31.26 | 11.8  | 1.85 | 0.18 |
|----|---|----|--------|-------|---|-------|-------|------|------|
| 9  | T | 51 | 38.37  | 10.51 | x | 31.26 | 11.8  | 1.83 | 0.18 |
| 10 | T | 51 | 42.221 | 10.41 | x | 30.65 | 11.78 | 2.56 | 0.18 |
| 11 | A | 32 | 46.302 | 10.67 | x | 31.51 | 12.06 | 1.53 | 0.18 |
| 12 | A | 51 | 46.911 | 10.5  | x | 31.52 | 11.97 | 1.51 | 0.18 |
| 13 | G | 51 | 51.588 | 9.05  | x | 30.85 | 10.85 | 2.44 | 0.15 |
| 14 | T | 51 | 51.772 | 9.05  |   | 30.85 | 10.85 | 2.44 | 0.15 |

The mapping positions were confirmed when using seed set on a secondary head in both locations and when using phenotypic data of F3 progeny of this populations the next year in two locations.

Example 3: Fine-Mapping of Rf Region in 1A and 1B

For further fine-mapping, 40 F2 individuals that were heterozygous in the QTL region were selected based on phenotype and genotype. A total of 2560 individual F3 plants were grown in the field at 2 locations. For each plant, seed set on the main head under a bag was measured. Additional SNP assays were developed to increase the marker density in the QTL interval. A total of 361 and 374 additional SNP markers were using in mapping the 1A and 1B region respectively. Table 2 provides exemplary SNP markers that were mapped in the region.

Marker-trait association using genetic maps of the chromosomes 1A and 1B, established on F2 and F3 genotyping data, were determined using R-QTL. A total of 1094 individuals with genotype and phenotype data were processed per location. The Rf loci could be further delimited to a region of about 1.9 cM for 1A (from 30.9 to 32.8 cM along chromosome 1A) and 1.25 cM for 1B (from 6.8 to 8.05 cM along chromosome 1B).

hybrid breeding. Single Rf factors do not fully restore in wheat. The observation of sufficient restoration achieved through the interaction of 2 or more Rf factors in heterozygous condition is important. FIG. 3 (F2-coarse mapping) and 4 (F3-fine mapping) demonstrate that not only the restorer loci are significantly influencing the restoration of fertility, but also their interaction. The interaction of Rf alleles at 1A and 1B loci is significant and accounts for 6.15% the phenotypic variation.

TABLE 3

The significance of marker-trait associations at the F3 generation when assuming a 2-QTL model with an interaction term, as calculated using R-QTL.

|       | LOD   | % phenotypic variance explained | p-value    |
|-------|-------|--------------------------------|------------|
| 1A    | 35.99 | 38.35                          | <2e-16 *** |
| 1B    | 21.97 | 20.56                          | <2e-16 *** |
| 1A:1B | 7.48  | 6.15                           | 9.77e-07 ***|

When all F2 individuals are classified according to the 1A and 1B peak markers and the seed set is plotted, it is apparent that individuals that are heterozygous for both 1A

TABLE 2

A: Exemplary markers in the fine-mapped region on 1A. Significant markers (highlighted with x) are examples of markers that are in the QTL support interval (LOD threshold >3; drop of 2 LODs from highest marker). The marker closest to the peak is marked with (v). Other markers residing outside the significant interval are indicated by 'left flanking region' (above) and 'right flanking region (below).

| SEQ ID NO | Rf donor allele | SNP position in SEQ ID NO | finemap map position (cM) | significant marker interval I | peak marker |
|-----------|-----------------|---------------------------|---------------------------|-------------------------------|-------------|
| 15 | T | 112 | 28.5  |   |   |
| 16 | C | 98  | 31.25 | x |   |
| 17 | G | 113 | 31.55 | x |   |
| 18 | C | 51  | 31.95 | x | v |
| 19 | G | 51  | 32.8  | x |   |
| 20 | C | 51  | 46.05 |   |   |

B: Exemplary markers in the fine-mapped region on 1B. Significant markers (highlighted with x) are examples of markers that are in the QTL support interval (LOD threshold >3; drop of 2 LODs from highest marker). The marker closest to the peak is marked with (v). Other markers residing outside the significant interval are indicated by 'left flanking region' (above) and 'right flanking region (below).

| SEQ ID NO | Rf donor allele | SNP position | finemap map position (cM) | significant marker interval I | peak marker |
|-----------|-----------------|--------------|---------------------------|-------------------------------|-------------|
| 21 | T | 51  | 6.1  |   |   |
| 22 | C | 51  | 7.1  | x |   |
| 23 | A | 51  | 7.3  | x |   |
| 24 | T | 51  | 7.35 | x | v |
| 25 | T | 108 | 8.05 | x |   |
| 10 | T | 51  | 8.1  |   |   |

Example 4: Interaction of Rf on 1A and 1B

The most important question in using native Rf alleles in wheat, is whether they act dominant, i.e., effectively restore when they are in heterozygous condition, as required for hybrid breeding. Single Rf factors do not fully restore in and 1B restorers set significantly more seed than the heterozygotes at each locus alone. The achieved restoration is higher than that of single homozygotes alone and slightly lower than that of 1A/1B homozygotes. This interaction was observed both at the F2 and the F3 generation (FIG. 5).

Example 5: Integration of the Fine Map with Partial Genome Sequence and Candidate Gene Identification Sequence of fine-mapped markers was used for Blasts to contigs and scaffolds of genome sequence of Chinese Spring (e.g. as available from TGAC: world wide web at tgac.ac.uk). Stringent BLAST and parsing criteria were applied to position the SNPs in the partial genome sequence, such as >98% sequence identity, alignment length of >158 bp, hit in 1A or 1B sequence, and additional criteria for non-aligning overhang. Scaffolds were ordered to the fine map (and additional genetic maps).

Example 6: Candidate Gene Validation

A mutagenized population of the restore line is constructed. Based on sequencing, mutant plants with an inactivating mutation in the Rf candidate gene are identified. The homozygous mutant plants and their wildtype segregants are screened for fertility restoration capacity. The plants that have a mutated gene no longer has restoring ability, confirming that the identified candidate gene is a functional Rf gene.

The coding sequence of the Rf candidate gene is cloned under the control of a constitutive UBIQUITIN promoter, or under control of its native promoter, in a T-DNA expression vector comprising a selectable marker, such as the bar gene. The resulting vector is transformed into a wheat line having no restoration capacity such as Chinese spring according to methods well known in the art for wheat transformation. The copy number of the transgene in the transgenic plant is determined by real time PCR on the selectable marker gene. The transformed plants with comprising the candidate Rf gene are tested for their capacity to restore fertility in progeny of a cross with a G-type cytoplasmic male sterility ("CMS") line. Plants transformed with a functional restorer gene are capable of restoring fertility against G-type cytoplasmic male sterility.

Plants comprising both the cloned 1A and 1B validated Rf genes achieve higher restoration than plants comprising either one.

The invention claimed is:

1. A method for producing a hybrid wheat seed comprising a functional restorer gene allele for wheat G-type cytoplasmic male sterility located on chromosome 1A (1A restorer gene allele) and a functional restorer gene allele for wheat G-type cytoplasmic male sterility located on chromosome 1B (1B restore gene allele), said method comprising:

(a) identifying at least one wheat plant comprising at least one marker allele linked to a functional restorer gene allele for wheat G-type cytoplasmic male sterility located on chromosome 1A (1A restorer marker allele) and at least one marker allele linked to a functional restorer gene allele for wheat G-type cytoplasmic male sterility located on chromosome 1B (1B restorer marker allele); and (b) crossing said plant comprising said 1A restorer marker allele and said 1B restorer gene allele with a wheat plant with G-type cytoplasmic male sterility, to obtain hybrid seed;

where said at least one marker allele linked to said functional restorer gene allele on chromosome 1A localizes within an interval on chromosome 1A which interval comprises and is flanked by two marker alleles, wherein said two marker alleles are selected from:

i) a C at a position corresponding to position 98 in SEQ ID NO: 16;
ii) a G at a position corresponding to position 113 in SEQ ID NO: 17;
iii) a C at a position corresponding to position 51 in SEQ ID NO: 18; or
iv) a G at a position corresponding to position 51 in SEQ ID NO: 19;

and wherein said at least one marker allele linked to said functional restorer gene allele on chromosome 1B localizes within an interval on chromosome 1B which interval comprises and is flanked by two marker alleles, wherein said two marker alleles are selected from:

e. a C at a position corresponding to position 51 in SEQ ID NO: 22;
f. an A at a position corresponding to position 51 in SEQ ID NO: 23,
g. a T at a position corresponding to position 51 in SEQ ID NO: 24; or
h. a T at a position corresponding to position 108 in SEQ ID NO: 25, or
i. a T at a position corresponding to position 51 in SEQ ID NO: 10.

2. A method for producing a fertile progeny plant from a G-type cytoplasmic male sterile wheat parent plant, said method comprising:

(a) providing a population of progeny plants or seeds obtained from crossing a female wheat parent plant with a male wheat parent plant, wherein the female parent plant is a G-type cytoplasmic male sterile wheat plant, and wherein the male parent plant comprises a functional restorer gene allele for wheat G-type cytoplasmic male sterility located on chromosome 1A (1A restorer gene allele) and a functional restorer gene allele for wheat G-type cytoplasmic male sterility located on chromosome 1B (1B restorer gene allele);

(b) selecting in said population a fertile progeny plant or seed comprising at least one marker allele linked to said functional restorer gene allele for wheat G-type cytoplasmic male sterility located on chromosome 1A (1A restorer marker allele) and at least one marker allele linked to said functional restorer gene allele for wheat G-type cytoplasmic male sterility located on chromosome 1B(1B restorer marker allele), wherein said progeny plant comprises said 1A restore gene allele and said 1B restorer gene allele; and optionally (c) propagating the fertile progeny plant or seed, where said at least one marker allele linked to said functional restorer gene allele on chromosome 1A localizes within an interval on chromosome 1A which interval comprises and is flanked by two marker alleles, wherein said two marker alleles are selected from:

i) a C at a position corresponding to position 98 in SEQ ID NO: 16;
ii) a G at a position corresponding to position 113 in SEQ ID NO: 17;
iii) a C at a position corresponding to position 51 in SEQ ID NO: 18; or
iv) a G at a position corresponding to position 51 in SEQ ID NO: 19;

and wherein said at least one marker allele linked to said functional restorer gene allele on chromosome 1B localizes within an interval on chromosome 1B which interval comprises and is flanked by two marker alleles, wherein said two marker alleles are selected from:

e. a C at a position corresponding to position 51 in SEQ ID NO: 22;
f. an A at a position corresponding to position 51 in SEQ ID NO: 23,
g. a T at a position corresponding to position 51 in SEQ ID NO: 24; or
h. a T at a position corresponding to position 108 in SEQ ID NO: 25, or
i. a T at a position corresponding to position 51 in SEQ ID NO: 10.

3. The method of claim 2, wherein said at least one marker allele linked to said functional restorer gene allele on chromosome 1A localizes to an interval on chromosome 1A comprising and flanked by the marker pair of SEQ ID NO: 16 and SEQ ID NO: 19 and/or wherein said at least one marker allele linked to said functional restorer gene allele on chromosome 1B localizes to an interval on chromosome 1B comprising and flanked by the marker pair of SEQ ID NO: 22 and SEQ ID NO: 25, wherein said marker of SEQ ID NO: 16 has a C at a position corresponding to position 98 in SEQ ID NO: 16, said marker of SEQ ID NO: 19 has a G at a position corresponding to position 51 in SEQ ID NO: 19, said marker of SEQ ID NO: 22 has a C at a position corresponding to position 51 in SEQ ID NO: 22, and said marker of SEQ ID NO: 25 has a T at a position corresponding to position 108 in SEQ ID NO: 25.

4. The method of claim 2, wherein said at least one marker allele linked to said functional restorer gene allele on chromosome 1A has:

a. a C at a position corresponding to position 98 in SEQ ID NO: 16;
b. a G at a position corresponding to position 113 in SEQ ID NO: 17;
c. a C at a position corresponding to position 51 in SEQ ID NO: 18;
d. a G at a position corresponding to position 51 in SEQ ID NO: 19;
or any combination thereof;
and/or wherein said at least one marker allele linked to said functional restorer gene allele on chromosome 1B has:
e. a C at a position corresponding to position 51 in SEQ ID NO: 22;
f. an A at a position corresponding to position 51 in SEQ ID NO: 23,
g. a T at a position corresponding to position 51 in SEQ ID NO: 24;
h. a T at a position corresponding to position 108 in SEQ ID NO: 25,
or any combination thereof.

5. The method of claim 2, wherein said at least one marker allele linked to said functional restorer gene allele on chromosome 1A has a C at a position corresponding to position 51 in SEQ ID NO: 18 and/or wherein said at least one marker allele linked to said functional restorer gene allele on chromosome 1B has a T at a position corresponding to position 51 in SEQ ID NO: 24.

6. The method of claim 2, wherein said 1A restorer gene allele and/or said 1B functional restorer gene allele is/are obtainable from USDA accession number PI 583676.

7. A method for producing a wheat plant comprising a functional restorer gene allele for wheat G-type cytoplasmic male sterility located on chromosome 1A and a functional restorer gene allele for wheat G-type cytoplasmic male sterility located on chromosome 1B, said method comprising
   a. crossing a first wheat plant comprising a functional restorer gene for wheat G-type cytoplasmic male sterility located on chromosome 1A and comprising a functional restorer gene for wheat G-type cytoplasmic male sterility located on chromosome 1B with a second wheat plant; and
   b. selecting a progeny plant comprising a functional restorer gene allele for wheat G-type cytoplasmic male sterility located on chromosome 1A and comprising a functional restorer gene allele for wheat G-type cytoplasmic male sterility located on chromosome 1B according to the method of claim 2.

8. A method for producing a wheat plant comprising a functional restorer gene allele for wheat G-type cytoplasmic male sterility located on chromosome 1A and comprising a functional restorer gene allele for wheat G-type cytoplasmic male sterility located on chromosome 1B, said method comprising
   a. crossing a first wheat plant homozygous for a functional restorer gene for wheat G-type cytoplasmic male sterility located on chromosome 1A and homozygous for a functional restorer gene for wheat G-type cytoplasmic male sterility located on chromosome 1B with a second wheat plant; and
   b. obtaining a progeny plant, wherein said progeny plant comprises a functional restorer gene allele for wheat G-type cytoplasmic male sterility located on chromosome 1A and a functional restorer gene allele for wheat G-type cytoplasmic male sterility located on chromosome 1B as described in claim 2.

9. A method for producing hybrid seed, said method comprising:
   a. providing a male wheat parent plant comprising at least one marker allele linked to a functional restorer gene for wheat G-type cytoplasmic male sterility located on chromosome 1A and at least one marker allele linked to a functional restorer gene for wheat G-type cytoplasmic male sterility located on chromosome 1B as described in claim 2, said male parent plant comprising said functional restorer gene allele for wheat G-type cytoplasmic male sterility located on chromosome 1A and said functional restorer gene for wheat G-type cytoplasmic male sterility located on chromosome 1B as described in claim 2;
   b. providing a female wheat parent plant that is a G-type cytoplasmic male sterile wheat plant;
   c. crossing said female wheat parent plant with said male wheat parent plant; and optionally
   d. harvesting seeds on said female wheat parent plant.

10. A method for determining the presence or absence or zygosity status of a functional restorer gene allele for wheat G-type cytoplasmic male sterility located on chromosome 1A and the presence or absence or zygosity status of a functional restorer gene allele for wheat G-type cytoplasmic male sterility located on chromosome 1B in a biological sample of a wheat plant or seed, said method comprising
   a. providing genomic DNA from said biological sample by obtaining tissue material from said plant or seed and preparing a crude extract or lysate therefrom, and
   b. analyzing said DNA for the presence or absence or zygosity status of at least one marker allele linked to said functional restorer gene for wheat G-type cytoplasmic male sterility located on chromosome 1A (1A restorer marker allele) and the presence or absence or zygosity status of at least one marker allele linked to said functional restorer gene for wheat G-type cytoplasmic male sterility located on chromosome 1B (1B restorer marker allele),
   wherein said at least one 1A restorer marker allele localizes within an interval on chromosome 1A which interval comprises and is flanked by two marker alleles, wherein said two marker alleles are selected from:
   i) a C at a position corresponding to position 98 in SEQ ID NO: 16;
   ii) a G at a position corresponding to position 113 in SEQ ID NO: 17;
   iii) a C at a position corresponding to position 51 in SEQ ID NO: 18; or
   iv) a G at a position corresponding to position 51 in SEQ ID NO: 19;
   and wherein said at least one 1B restorer marker allele localizes within an interval on chromosome 1B which interval comprises and is flanked by two marker alleles, wherein said two marker alleles are selected from:
   e. a C at a position corresponding to position 51 in SEQ ID NO: 22;
   f. an A at a position corresponding to position 51 in SEQ ID NO: 23,
   g. a T at a position corresponding to position 51 in SEQ ID NO: 24; or
   h. a T at a position corresponding to position 108 in SEQ ID NO: 25, or
   i. a T at a position corresponding to position 51 in SEQ ID NO: 10.

* * * * *

```
                         SEQUENCE LISTING

<160> NUMBER OF SEQ ID NOS: 25

<210> SEQ ID NO 1
<211> LENGTH: 201
<212> TYPE: DNA
<213> ORGANISM: Triticum aestivum

<400> SEQUENCE: 1
gttatgactc ctttatgtac atcttggcgg cgtcttgttt taggtaccgg cagcaccaag      60
gagtttctta gaatcattgt tgtgcaaaat tggcctcgcc rtttcctctt cttttttcaa    120
tggagaagcc gctgcaggtg cttgtggatt acgtatgata ctcgctccca gtgcaagttg    180
tctggaggtt tttgaagtca a                                              201

<210> SEQ ID NO 2
<211> LENGTH: 101
<212> TYPE: DNA
<213> ORGANISM: Triticum aestivum

<400> SEQUENCE: 2
ctgagtagct tggagtcgca ggccacgatc ttcaccttgc ccacctgctc rgtcgtctcc     60
tcgttcttga actgcgcgtc cgtcaggatg aatgtccaca c                        101

<210> SEQ ID NO 3
<211> LENGTH: 101
<212> TYPE: DNA
<213> ORGANISM: Triticum aestivum

<400> SEQUENCE: 3
agcgttccta ataaacaatt ttttatacgt ctagcctaga actaatcgcc yggataactg     60
cggtaatctg gactcattct ctgtcacaat taccatgtcc g                        101

<210> SEQ ID NO 4
<211> LENGTH: 101
<212> TYPE: DNA
<213> ORGANISM: Triticum aestivum

<400> SEQUENCE: 4
aatctcaatc tgggcggcaa gacgaagcgg agcaactacg cggtggacgc mgacattgtc     60
```
caggacgtca agagatttca gggcaacgtc ttcttggcca a              101

<210> SEQ ID NO 5
<211> LENGTH: 101
<212> TYPE: DNA
<213> ORGANISM: Triticum aestivum

<400> SEQUENCE: 5
ctgaaggaaa gggatccatg gtaatacac cgtgtacatt ctaggggtc rtgtgacagc    60 agaatcaact taattttga cgagcaacca aataccgact g              101

<210> SEQ ID NO 6
<211> LENGTH: 101
<212> TYPE: DNA
<213> ORGANISM: Triticum aestivum

<400> SEQUENCE: 6
acctttatcg tctcttggta ctgtgatatt gagactggta agtaaggttc rgttggtgct    60
taatcaccat aggccatagc atgggccctg tcctagtgta a              101

<210> SEQ ID NO 7
<211> LENGTH: 101
<212> TYPE: DNA
<213> ORGANISM: Triticum aestivum

<400> SEQUENCE: 7
cggcacaacc caagcaaacc acccaatgca cgtgccttca gctcctctgg yacgctcttc    60
aagaggctct ctgcttcttc cagaaggcca acactcccat a              101

<210> SEQ ID NO 8
<211> LENGTH: 101
<212> TYPE: DNA
<213> ORGANISM: Triticum aestivum

<400> SEQUENCE: 8
tacatgatgg tgttatgtat caaccaacat tacagtgcgc ttgtcgactc mtggtccttt    60
ctgactgtca atctcatgag agaattggct cgagaatttc g              101

<210> SEQ ID NO 9
<211> LENGTH: 101
<212> TYPE: DNA
<213> ORGANISM: Triticum aestivum

<400> SEQUENCE: 9
tccatctttt tgttgagatt tactgaagaa cagccgtggc aaggcgctcc ygtgcaaaaa    60
ttcgtgctct cgtttgcctc accagcccct gttctgtttg t              101

<210> SEQ ID NO 10
<211> LENGTH: 101
<212> TYPE: DNA
<213> ORGANISM: Triticum aestivum

<400> SEQUENCE: 10
tccttcagac atcgaacaca tcatcataca tgtcggcgtc ccagtccgcg ycgtcgatat    60
aatcctccat gtcatcaaac tcggcatcct cgtcgtcgtc g              101

<210> SEQ ID NO 11
<211> LENGTH: 250
<212> TYPE: DNA
<213> ORGANISM: Triticum aestivum

<400> SEQUENCE: 11

```
accaggtgcc gcttgaaggc agatcagaag argttatgac tccttcatgt acatcttggc    60
cgcgtcttgt tttaggcacc ggcggcagca gcagcaggga gtctcttaga accattgttg   120
tgcaaaactg gccttgccgt ctcctcttcc ttttttcaat ggagaagctg ccgcaggtgc   180
ttgtggatta catttcatat gatactcact cccaccagcg caagttgtct ggaggttttt   240
gaagtcaacg                                                         250
```

<210> SEQ ID NO 12
<211> LENGTH: 101
<212> TYPE: DNA
<213> ORGANISM: Triticum aestivum

<400> SEQUENCE: 12

```
ggcagagccg gtcgacggag aggagcgcca ttcgacgcgt cttccgcaat rtgtttgcct    60
gcttcggccg cggccattcg gcgagctccc acgcttcgtc c                       101
```

<210> SEQ ID NO 13
<211> LENGTH: 93
<212> TYPE: DNA
<213> ORGANISM: Triticum aestivum

<400> SEQUENCE: 13

```
ttccggcagg tcttaaccaa ttccaatttt cattatccaa gcatagcact kaatcttgca    60
tttratcata agcttgttga ctggctaata ctr                                93
```

<210> SEQ ID NO 14
<211> LENGTH: 101
<212> TYPE: DNA
<213> ORGANISM: Triticum aestivum

<400> SEQUENCE: 14

```
ctgaaggaaa gggatccatg ggtaatacac cgtgtacatt ctaggggtc rtgtgacagc     60 agaatcaact taattttga cgagcaacca aataccgact g                       101
```

<210> SEQ ID NO 15
<211> LENGTH: 146
<212> TYPE: DNA
<213> ORGANISM: Triticum aestivum

<400> SEQUENCE: 15

```
tccagcacgt acatagcgac ttttattgtc ggttgaataa tatgttatcc tcgtcgtgag    60
ttgaatagta gaactacaca cgtggaattt acagatagct acttctttcg tycgaaaaaa   120
cttgtcccaa acttgttcct taaacg                                       146
```

<210> SEQ ID NO 16
<211> LENGTH: 1113
<212> TYPE: DNA
<213> ORGANISM: Triticum aestivum
<220> FEATURE:
<221> NAME/KEY: misc_feature
<222> LOCATION: (937)..(945)
<223> OTHER INFORMATION: n is a, c, g, or t

<400> SEQUENCE: 16

```
aaattgtgta caagaagctg aaggagaagg cagaccagtt tgtggccaga gggctggtca    60
ggacgccgga cagcaaatct aagatcgatg ggggcgayga cgtgttcatc ggagacatta   120
```

```
gggatcctgg gagcattgcg ccggcgatcg acggcattga cgcgctcatc atcctcacca      180
gtggggtccc gaagatgaag ccagggtttg atcctagcaa aggggggtcgg cccgagtttt      240 acttcgagga agggtctgat cctgagcagg tggattggat aggccaaaag aaccaaatcg      300
acgctgccaa gagcattggt gtaaagcaga tagttttggt tggatccatg ggtggaacag      360
atctcaacca tccattaaac aagcttggga atgggaatat actggtgtgg aaacggaagg      420
cagaacagta cctagcggac tctggtgtac catatacaat tataagggct ggaggactac      480
aagacaaaga tggtggtgtg cgtgagttga ttgttggaaa ggatgacgag atcttgaaga      540
cggaaacaaa aactattgcc agggcagatg ttgcagaagt ttgcatacag gccttgctat      600
ttgaggaagc aaagttcaag gcatttgatc tggcttcaaa acctgaaggt gaaggaacac      660 cgacgcacaga ttttaagtct gtttttgcac aaattgctac tcgcttctaa gaagacaaga      720
tcattctggc caatgaaatg gggacagttt tttaattagg cgatatggaa tttgtaccgg      780
gtcaggaggc tcctcatctg atcaagtagc aaaagtaggg aagcatgcac cttgttattg      840
agcagaagaa gcagcagatc gttgtgcttt gagagaagag ttctgaggat ttgggctatg      900
aaagaagagt agtgagactg gtgttgatgt aaactannnn nnnnncttct tgttgctttg      960
ttcccaacgt cggacatggt aattgtgaca gagaatgagt ccagattacc gcagttatcc     1020
aggcgattag ttctaggcta gacgtataaa aaattgttta ttaggaacgc ttgcctgggt     1080
ttcaacatta atacggttcc taattgaatt gat                                  1113

<210> SEQ ID NO 17
<211> LENGTH: 185
<212> TYPE: DNA
<213> ORGANISM: Triticum aestivum

<400> SEQUENCE: 17
tatgattgcg gccatgtaga gtagctcctc ttcgtcggac gaggaatcca ggaagtattg       60
ccaggccaag ctgcgacggc ggcggctcat ctcgttgcgg ggagacaacg gakagatggg      120
gaatgggatg tggaatggag acagagccag gggtgtgtga gtgtgtgtgt gagagagaga      180
gacag                                                                  185

<210> SEQ ID NO 18
<211> LENGTH: 101
<212> TYPE: DNA
<213> ORGANISM: Triticum aestivum

<400> SEQUENCE: 18
cgtgtcctcc ctctacctct tgaataccac ctcatgttgt tgatgccgcc mtccatcggc       60
accggagagc atcagcacct gatggtgcca ttgctggctc c                         101

<210> SEQ ID NO 19
<211> LENGTH: 101
<212> TYPE: DNA
<213> ORGANISM: Triticum aestivum

<400> SEQUENCE: 19
agatgcctag cgcggggctg gaggcggggt cgaacaaggt ggacgtggcc rtcgacctcg       60
ggaacccgct cctcaaccgc accgtcgacg gcttcctcaa g                         101

<210> SEQ ID NO 20
<211> LENGTH: 101
<212> TYPE: DNA
<213> ORGANISM: Triticum aestivum
```

-continued

```
<400> SEQUENCE: 20
aatctcaatc tgggcggcaa gacgaagcgg agcaactacg cggtggacgc mgacattgtc        60
caggacgtca agagatttca gggcaacgtc ttcttggcca a                           101

<210> SEQ ID NO 21
<211> LENGTH: 101
<212> TYPE: DNA
<213> ORGANISM: Triticum aestivum

<400> SEQUENCE: 21
tccatctttt tgttgagatt tactgaagaa cagccgtggc aaggcgctcc ygtgcaaaaa        60
ttcgtgctct cgtttgcctc accagcccct gttctgtttg t                           101

<210> SEQ ID NO 22
<211> LENGTH: 101
<212> TYPE: DNA
<213> ORGANISM: Triticum aestivum

<400> SEQUENCE: 22
tcatgtggct tgccatgttc cagaacatgc tgaacaacat agttaccata ytgatcttga        60
gccagcaagc aaacagactg gagaatctca tccatcatta t                           101

<210> SEQ ID NO 23
<211> LENGTH: 101
<212> TYPE: DNA
<213> ORGANISM: Triticum aestivum

<400> SEQUENCE: 23
ccaattatca acctcctgac tgtgagggaa acaaagggaa tagatagatt rctccagtac        60
acatcacgag gttctggagc ccattcagtc agccaaaggg t                           101

<210> SEQ ID NO 24
<211> LENGTH: 101
<212> TYPE: DNA
<213> ORGANISM: Triticum aestivum

<400> SEQUENCE: 24
atgaagcccg ggttcgatcc tagcaagggt ggacggccgg agttttactt ygaggaaggg        60
tctgatcctg agcaggtgga ttggataggc caaaagaacc a                           101

<210> SEQ ID NO 25
<211> LENGTH: 293
<212> TYPE: DNA
<213> ORGANISM: Triticum aestivum

<400> SEQUENCE: 25
ttggctggta gcactgactg gtcaaacctc tatatatagc ttatccaatg gaatacatat        60
tgtccgacgt ctctcttgtc aaaagtatta gtggaacatt tgctcgawgc ctttactaga       120
cccgtccaaa tgtctggtag tacacacatg aaatggaagt ggtgtcgggt aaacataaac       180
tggaagtaaa taaatttaac gtctctcttc tcctttttcgc tttcgcattg tctcttttca      240
tcaacaatga cccgcgaaga taatcatcgg gcacatcctt tggttcctcc tga             293
```